United States Patent
Heyl et al.

(10) Patent No.: US 10,786,210 B1
(45) Date of Patent: Sep. 29, 2020

(54) SYSTEM FOR MONITORING INCONTINENT PATIENTS

(71) Applicant: BioLink Systems, LLC, Covington, KY (US)

(72) Inventors: Ken Heyl, Birminghan, AL (US); Roger King, Hamilton, OH (US)

(73) Assignee: BioLink Systems, LLC, Covington, KY (US)

( * ) Notice: Subject to any disclaimer, the term of this patent is extended or adjusted under 35 U.S.C. 154(b) by 0 days.

(21) Appl. No.: 16/881,361

(22) Filed: May 22, 2020

Related U.S. Application Data

(63) Continuation of application No. 16/522,050, filed on Jul. 25, 2019, now Pat. No. 10,713,372.

(51) Int. Cl.
| | |
|---|---|
| *A61B 5/00* | (2006.01) |
| *G06F 3/14* | (2006.01) |
| *G06F 3/0484* | (2013.01) |
| *G08B 13/196* | (2006.01) |

(52) U.S. Cl.
CPC ............ *A61B 5/743* (2013.01); *A61B 5/7435* (2013.01); *G06F 3/0484* (2013.01); *G06F 3/1454* (2013.01); *G08B 13/19682* (2013.01)

(58) Field of Classification Search
CPC .............. G06F 3/04817; G06F 3/0484; G06F 3/04842; G06F 3/1454; G06F 3/147; G08B 13/19678; G08B 13/19682; G08B 13/19686; G08B 13/19693; H04N 21/43615; H04N 21/42202; H04N 21/42204; A61B 5/00; A61B 5/0002; A61B 5/0022; A61B 5/742; A61B 5/7425; A61B 5/743; A61B 5/7435; A61B 5/7445; A61B 5/745
See application file for complete search history.

(56) References Cited

U.S. PATENT DOCUMENTS

| | | |
|---|---|---|
| 7,053,781 B1 | 5/2006 | Haire et al. |
| 7,977,529 B2 | 7/2011 | Bergman et al. |
| 7,996,148 B2 | 8/2011 | Bergman et al. |
| 8,145,422 B2 | 3/2012 | Bergman et al. |
| 8,788,195 B2 | 7/2014 | Bergman et al. |
| 9,107,776 B2 | 8/2015 | Bergman et al. |
| 9,224,102 B2 | 12/2015 | Bergman et al. |
| 9,283,123 B2 | 3/2016 | Bergman et al. |
| 9,314,381 B2 | 4/2016 | Bergman et al. |

(Continued)

*Primary Examiner* — Van T Trieu
(74) *Attorney, Agent, or Firm* — Chris Tanner; FYPA PLLC

(57) ABSTRACT

A method of adding sensing of moisture and other characteristics into a garment such as a diaper, incontinence garment, brief, or underwear is disclosed. The primary design intent is optimal moisture detection, low per unit cost, and wide-scale data analysis of groups of patients. The embodiments place various forms of electrodes within a garment, and measuring the electrical properties of the electrodes to determine if the garment has contacted moisture. The embodiments herein could be used for sensing incontinence, sensing perspiration, and detecting failure of protective garments, among other purposes. The target moisture is urine and feces; however, other sources of body moisture can also be sensed. A specialized mesh network achieves accuracy of the information obtained, as well as redundancy and timely updating of that information.

19 Claims, 25 Drawing Sheets

(56) References Cited

U.S. PATENT DOCUMENTS

| | | | |
|---|---|---|---|
| 9,646,073 B2 | 5/2017 | Bergman et al. | |
| 9,665,639 B2 | 5/2017 | Bergman et al. | |
| 9,713,554 B2 | 7/2017 | Bergman et al. | |
| 9,913,608 B2 | 3/2018 | Bergman et al. | |
| 2015/0031978 A1* | 1/2015 | Saroka | A61B 5/053 600/389 |
| 2016/0095758 A1 | 4/2016 | Haire et al. | |
| 2016/0284206 A1* | 9/2016 | Boettcher | G01N 33/5008 |
| 2017/0097621 A1* | 4/2017 | Ackmann | G05B 15/02 |
| 2017/0330430 A1* | 11/2017 | Goodfield | G08B 5/36 |
| 2019/0013960 A1* | 1/2019 | Sadwick | H04L 12/2838 |
| 2019/0074085 A1* | 3/2019 | Caffarel | G16H 50/30 |
| 2019/0209022 A1* | 7/2019 | Sobol | A61B 5/1112 |

\* cited by examiner

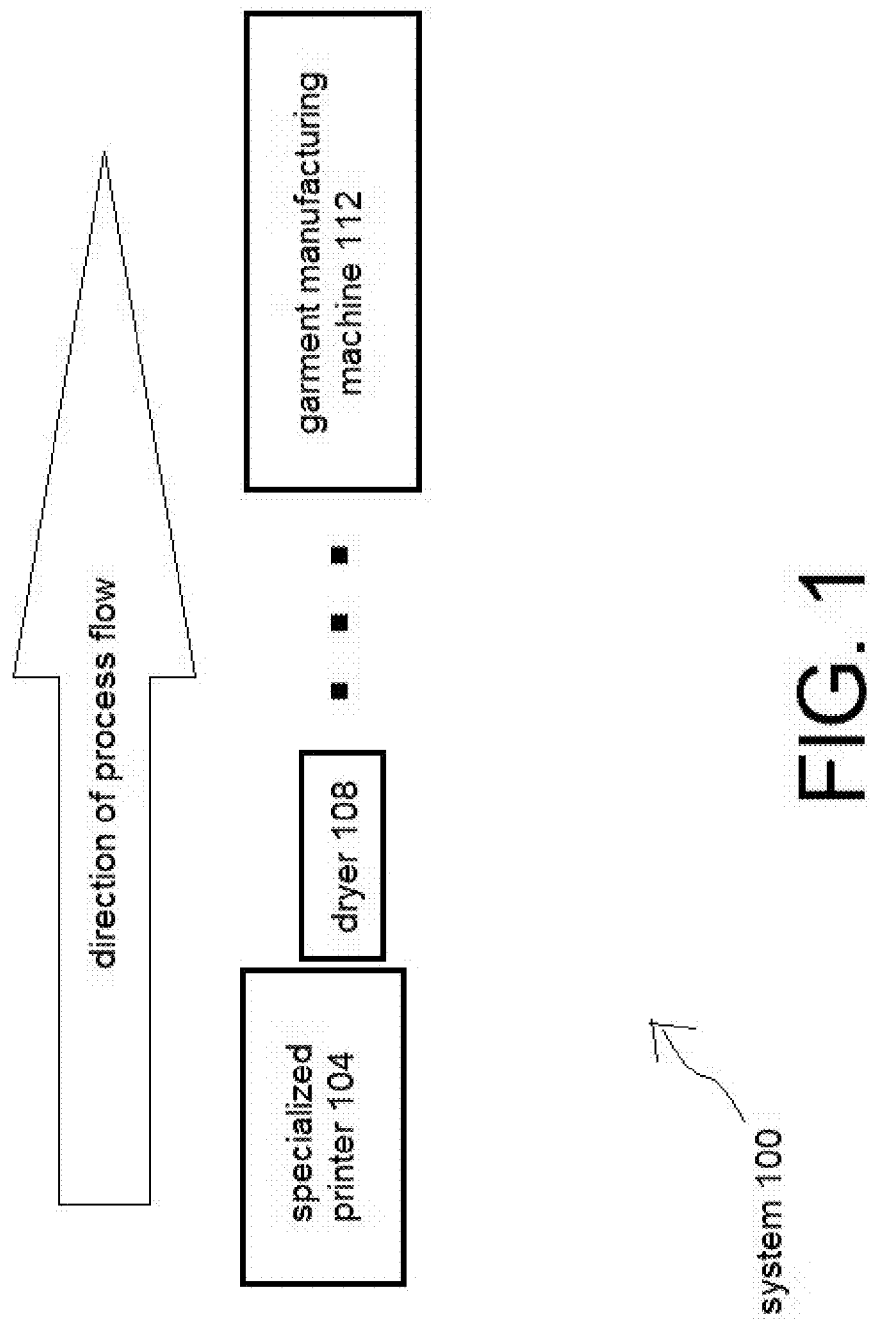

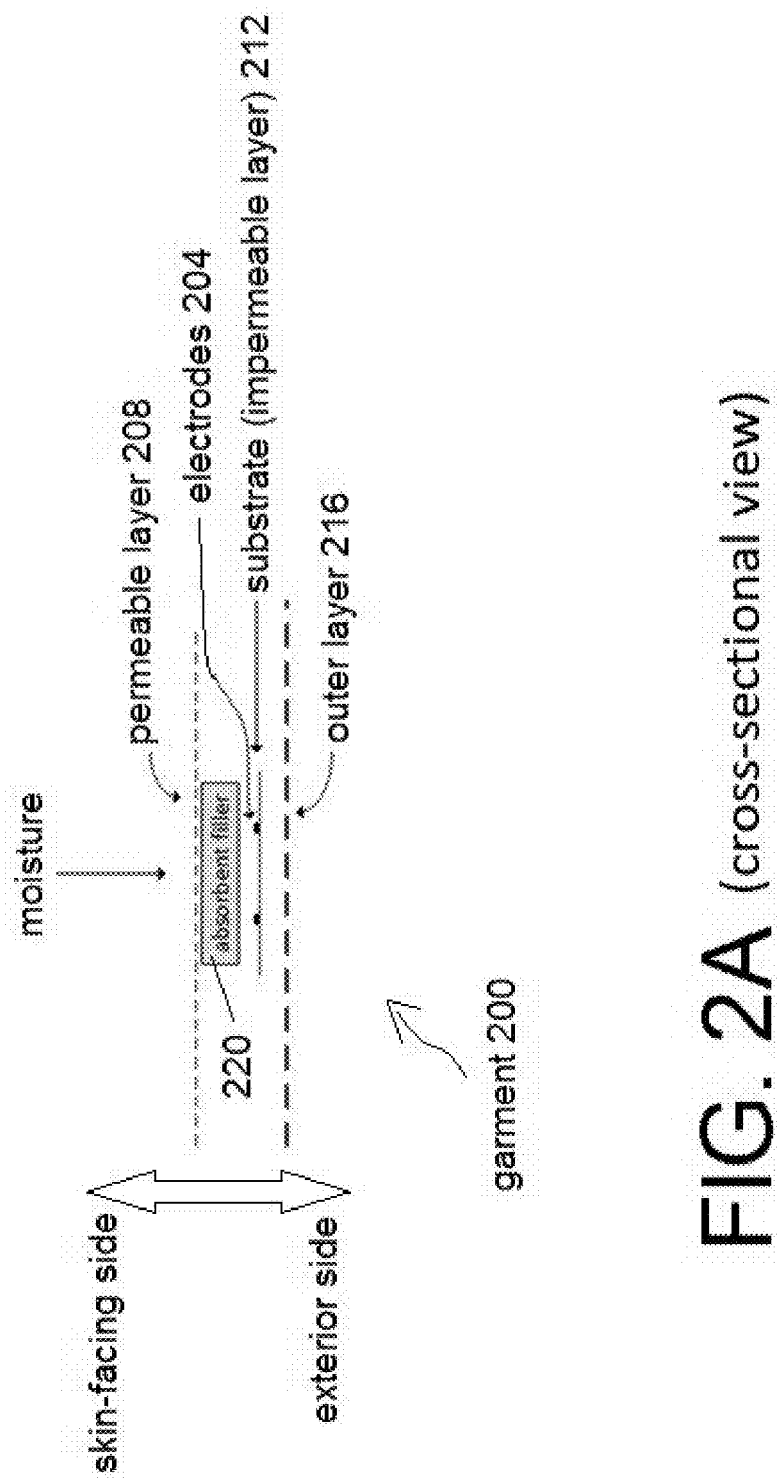
FIG. 2A (cross-sectional view)

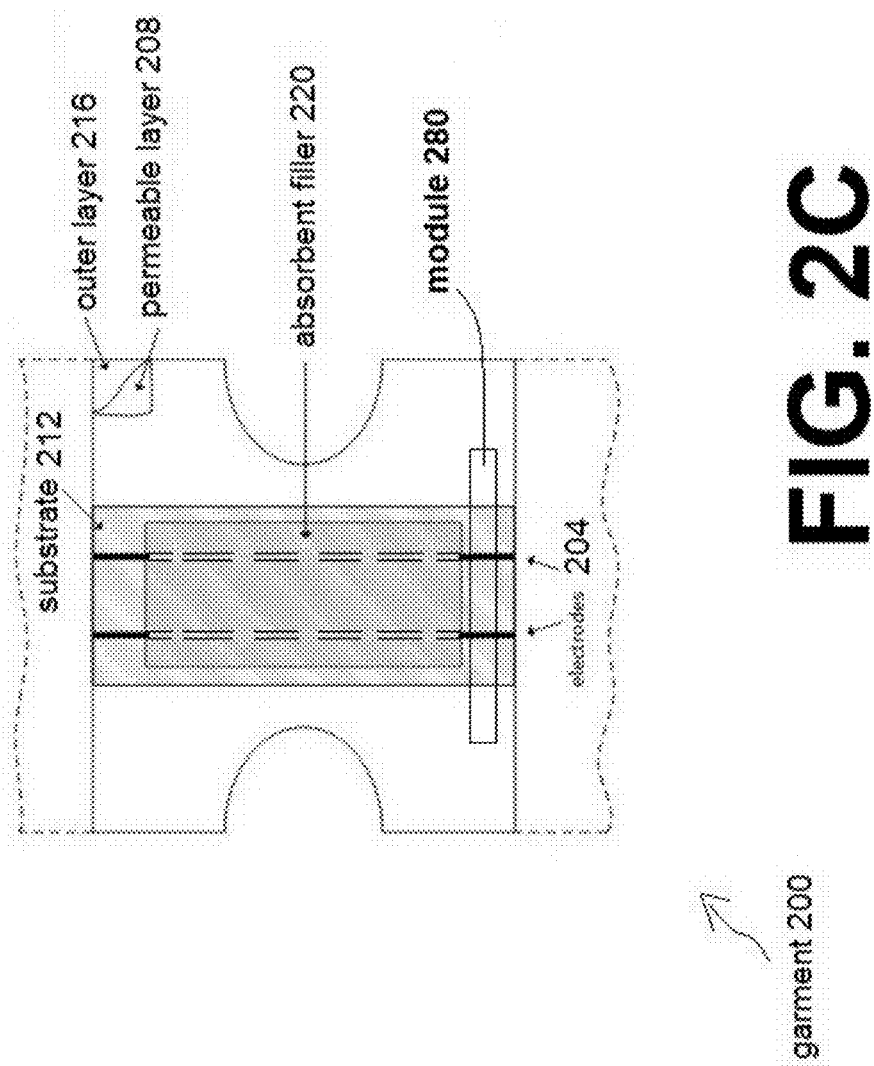

FIG. 4E

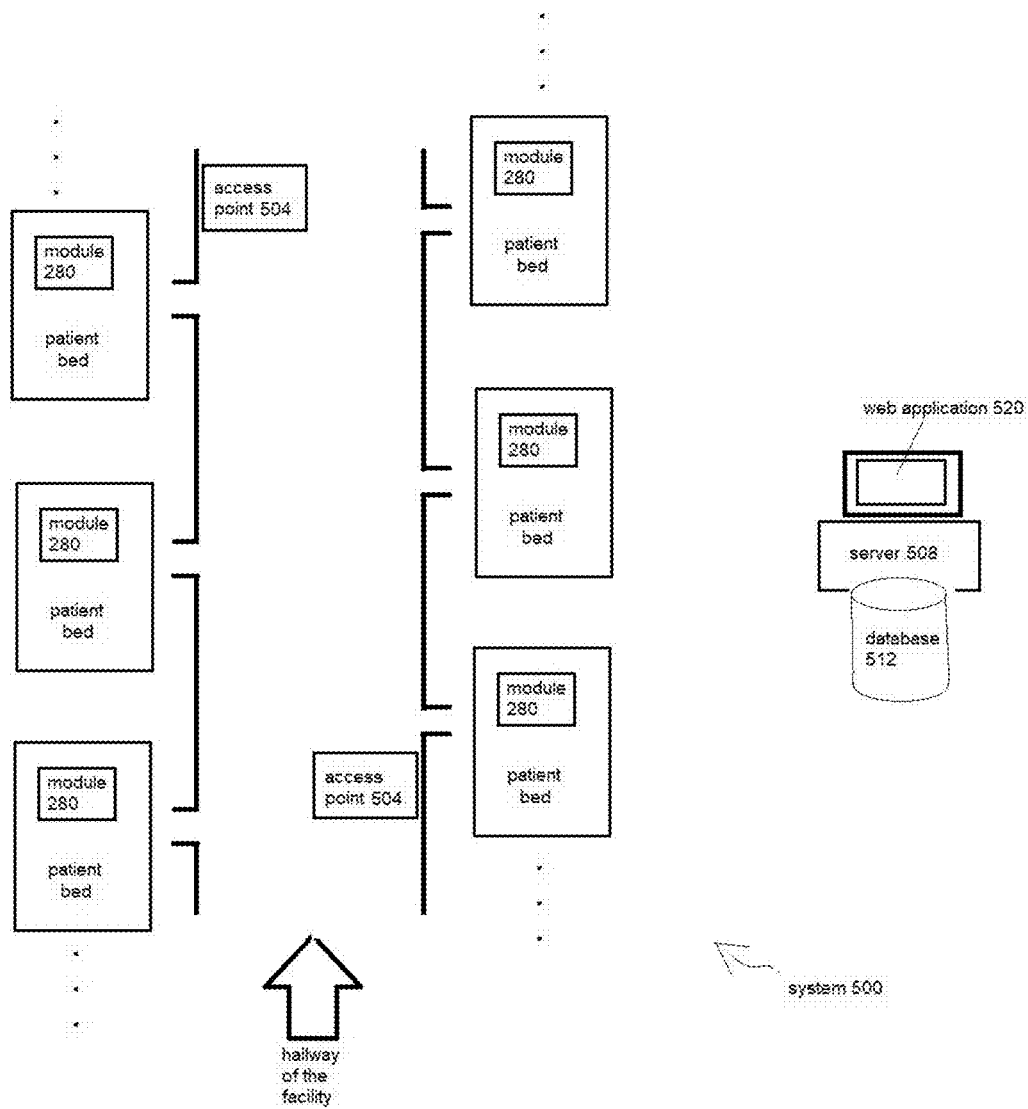
FIG. 5A topology

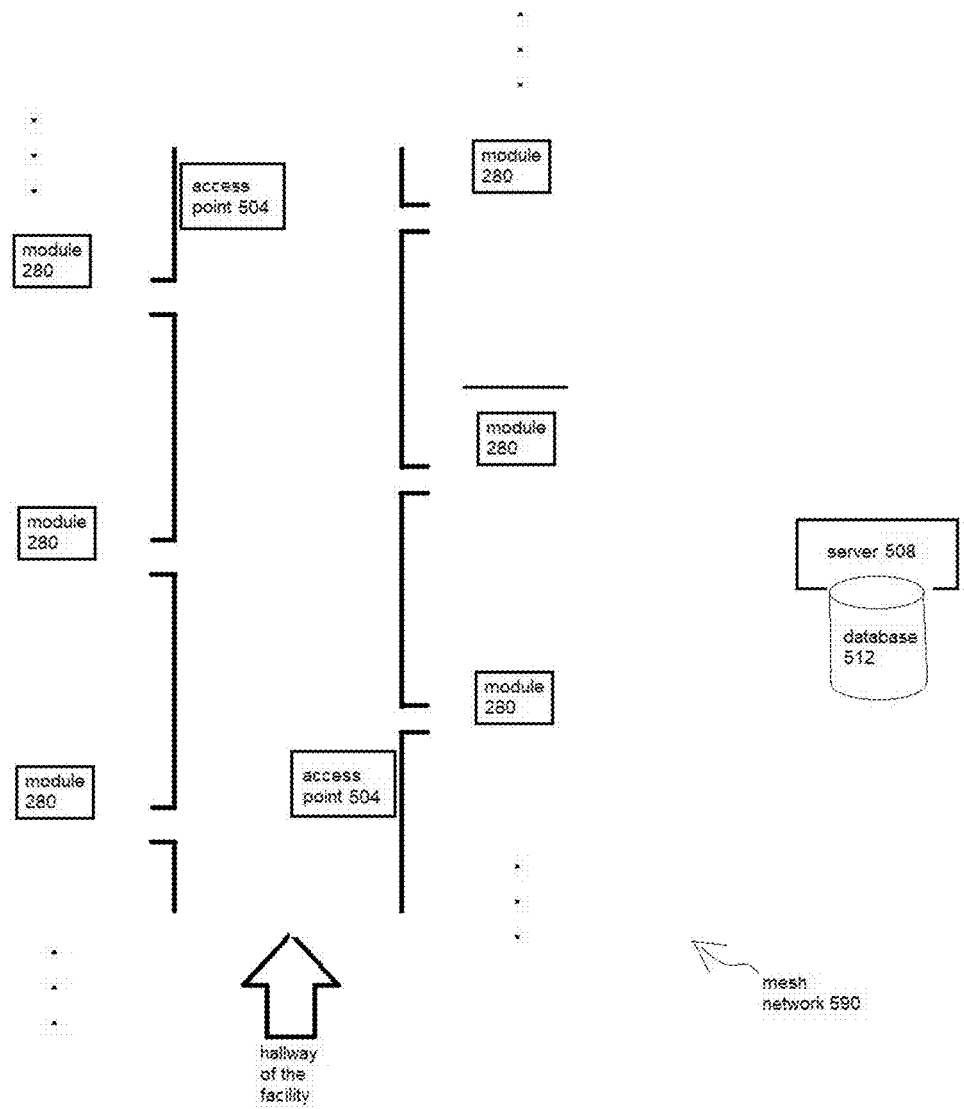
FIG. 5C (mesh network)

| stduser | Residents | Modules | Pagers | | | Logout |
|---|---|---|---|---|---|---|

Modules

| Resident | Moisture | Temperature | Position | Hygiene | Hydration | Fecal Impact | Contact |
|---|---|---|---|---|---|---|---|
| 100 | 72 | 93.5 | Back | OK | OK | OK | Connected |
| 200.0 | 71 | 93.8 | Back | OK | OK | OK | Connected |
| 300 | 0 | 94.5 | Back | OK | OK | OK | Connected |
| 400 | 0 | 92.9 | Back | OK | OK | OK | Connected |
| 500 | 0 | 94.9 | Back | OK | OK | OK | Connected |

GUI 604

FIG. 6A (standard user access)

| admin | Staff | Residents | Modules | Pagers | Access Points | System | Logout |

| MAC Address | Resident | Moisture | Temperature | Position | Hygiene | Hydration | Fecal Impact | Contact | Modify |
|---|---|---|---|---|---|---|---|---|---|
| C0:4E:EF:87:67:90 | 100 | 72 | 93.5 | Back | OK | OK | OK | Connected | Modify |
| C0:A4:F5:36:F4:8B:83 | 200-E | 72 | 93.8 | Back | OK | OK | OK | Connected | Modify |
| F8:40:A5:1E:9A:E6 | 300 | 0 | 94.5 | Back | OK | OK | OK | Connected | Modify |
| C0:A8:F0:3D:8B:7C | 400 | 0 | 92.9 | Back | OK | OK | OK | Connected | Modify |
| C0:B1:F5:87:E6:B2 | 500 | 0 | 94.9 | Back | OK | OK | OK | Connected | Modify |

620 ↗

GUI 608

FIG. 6B (supervisor access)

| Moisture | Temperature | Posi |
|---|---|---|
| 72 | 93.1 | Ba |
| 71 | 93.8 | Ba |
| 0 | 102.7 (0 m) | Ba |
| 0 | 92.7 | Ba |
| 0 | 94.2 | Ba |

FIG. 6C (Temperature Warning)

| Moisture | Temperature | Posi |
|---|---|---|
| 72 | 93.1 | Ba |
| 71 | 93.8 | Ba |
| 0 | 102.7 (0 m) | Ba |
| 0 | 92.7 | Ba |
| 0 | 94.2 | Ba |

FIG. 6D (Hover)

Do you want to acknowledge the temperature alert for 300?

| Resident | Moisture | Temperature | Position | Hygiene | Hydration | Fecal Impact | Contact |
|---|---|---|---|---|---|---|---|
| 100 | 72 | 93.5 | Back | OK | OK | OK | Connected |
| 200-B | 71 | 93.8 | Back | OK | OK | OK | Connected |
| 300 | - | - | - | - | - | - | Unknown |
| 400 | 0 | 92.9 | Back | OK | OK | OK | Connected |
| 500 | 0 | 94.9 | Back | OK | OK | OK | Connected | stduser  Residents  Modules  Pagers                                    Logout

Modules

FIG. 7D (module access)

scanning the one or more electrodes thereby detecting whether continuity exists between the one or more contacts connected to the one or more electrodes,  a low resistance measurement indicating multiple contacts are on one electrode, 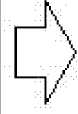 an open circuit measurement indicating the contact is not on the electrode or the electrodes are dry, and a measurement value consistent with moisture indicating the contacts are on multiple electrodes and that moisture is present

FIG. 9

SYSTEM FOR MONITORING INCONTINENT PATIENTS

BACKGROUND OF THE INVENTION

A shortcoming of existing embodiments of conductive garments is that incorporating conductive threads or fibers into clothing or other textile or paper products may not be compatible with manufacturing in high volume. Further, managing facilities that have large amounts of patients, some of whom may be incontinent, and employees can be difficult.

To address these and other issues, a system and method for inclusion of conductive inks and other materials into clothing or other textile or paper products for the purpose of sensing moisture is discussed, especially where that system is compatible with high volume manufacturing systems. Additionally, a mechanism for tracking and collecting medical information about the patients, especially incontinence information, is also discussed.

SUMMARY OF THE INVENTION

A method of adding sensing of moisture and other characteristics into a garment such as a diaper, incontinence garment, brief, or underwear is disclosed. The primary design intent is optimal moisture detection and low per unit cost, including designs for mass manufacturing considerations. The embodiments place various forms of electrodes within a garment, and then, while the garment is worn, measuring the electrical properties of the electrodes to determine if the garment has contacted moisture. A sensor module is located within the garment, and the electrical properties of the sensor element are measured to determine if the garment has contacted moisture. Moisture can include but is not limited to bodily fluids but can also include fluids from the environment. The embodiments herein could be used for sensing incontinence, sensing perspiration, and detecting failure of protective garments.

The target moisture is urine and feces; however, other sources of body moisture can also be sensed. Additional computer-implemented analysis capabilities can be added by selecting particular electrodes or additional materials that may react with chemical components of the specific moisture. A specialized mesh network achieves accuracy of the information, as well as redundancy and timely updating of the information.

The embodiments herein include detection of moisture in an item worn by or placed near a person, and systems and methods for manufacturing the same. Most often this will be a disposable diaper, incontinence garment, brief, or underwear, although embodiments of the combination\system disclosed herein could potentially be used in pads and bandages, and detect types of moisture other than incontinence.

A system comprises a plurality of access points which receive the resident data and send the data to the server. The information for each resident is transmitted over Bluetooth approximately every e.g. 3 seconds, although this time-interval can be adjusted. The server analyzes the data and continually updates a database with the current resident information. A web interface displays the information that it reads from the database.

As stated, the module transmits biometric data at predetermined intervals, e.g. every 3 seconds. While powered on, the module will continue to send biometric data to the server, through the access points. The server maintains a timestamp of the last time data was received from that module. If a set amount of time elapses without receiving data from a module, the server marks that module as 'Inactive', and can potentially also send an alert or a page.

It is also possible to track movement of the modules as the residents wearing the modules are e.g. walking down a hall and being handed off to the next access point. The access points can track a resident by location in building or if they left the building, and can know that wearer of the module is not a nurse but instead is a resident. So tracking is another thing that that can be accomplished by knowing which access point reported, and where they are within the mesh network.

The access points are receiving their main power from the wall, so battery-charging and power considerations are not an issue. Further, in the event of catastrophic power issues, all workers and facilities can always check the diaper on the invention the old-fashioned way, by looking, or by using existing on-premise hand-held devices e.g. a smart phone. Thus, the embodiments herein are effective whether they're under power or not.

One advantage of the system is it always knows exactly what is occurring inside of any patient's diaper. Statistically, the system gives management the ability to understand what is going on within every garment in the entire facility, all at once.

BRIEF DESCRIPTION OF THE DRAWINGS

FIG. 1 shows an arrangement of a garment-manufacturing system according to an embodiment;

FIG. 2A shows a cross-sectional view of an embodiment of a garment;

FIG. 2C shows a sensor module attached to the garment shown in FIGS. 2A and 2B;

FIG. 4E shows a desktop GUI used within the embodiments herein;

FIGS. 5A, 5B, and 5C show example communication topologies;

FIGS. 6A, 6B, 6C, 6D, and 6E show example GUIs;

FIGS. 7A, 7B, 7C, and 7D show various status GUIs;

FIG. 9 is a flowchart showing a method of using the embodiments.

DETAILED DESCRIPTION OF THE PREFERRED EMBODIMENTS

Figure 2B:
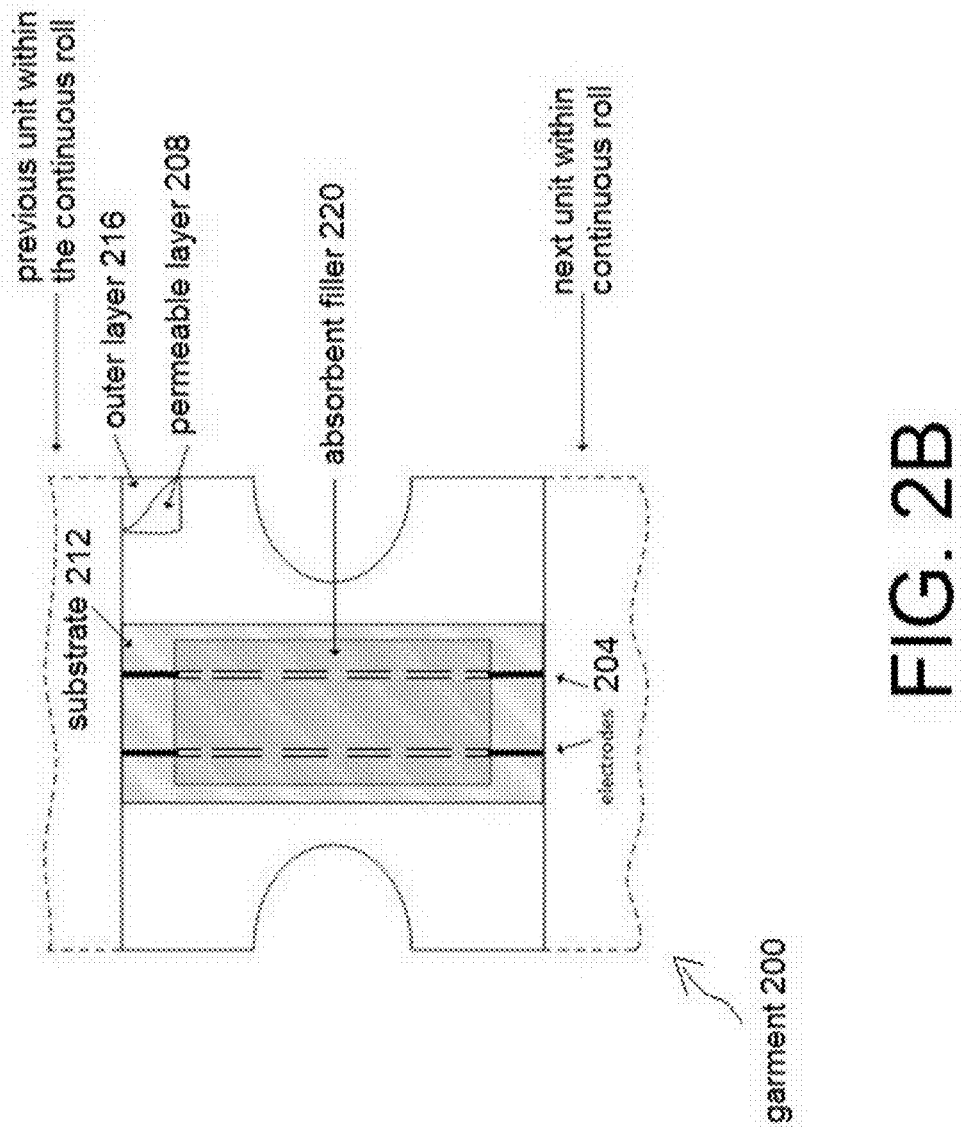
FIG. 2B shows a parallel pattern integrated within a garment in a continuous roll method.

The following definitions will apply throughout this disclosure.

Garment: a diaper, incontinence device, brief, underwear, or other article of clothing, bandage, or pad containing electrodes. Within this disclosure, the expression "diapers", "briefs", or "disposable underwear" will be used interchangeably with the phrase "incontinence garment".

Module: an electronic device attached to the garment and containing a power source, various sensors, and communication circuit.

Electrode: a conductive path connecting the module to a location within the garment being sensed. Within the embodiments herein, two or more electrodes may be used. The electrodes may be the same or different material. Electrodes may provide both connection and sensing functions.

Moisture: a deposition of a single or combination of bodily or other fluids. External sources of moisture may also be sensed.

Substrate: the layer that contains the electrodes.

Contacts: a type of electrical connection to the electrodes, e.g. potentially a place to locate wires or sensors.

Binder or Enhancements: materials that may be added to the garment to improve wetting, adhesion, durability, resistance to oxidation, flexibility and resistance to cracking, or to aid in manufacturing.

FIG. 1 shows a (simplified) arrangement of a system 100, in which one or more specialized printers 104, each with a dryer 108 at the back end, work in conjunction with a garment manufacturing machine 112 to create various embodiments of the garment 200 discussed herein. In an embodiment, the specialized printer 104 is a flexographic printer, although other types of printers may also be used. The garment manufacturing machine 112 is intentionally shown to be separated from the printer 104 and dryer 108 by ellipses ( . . . ), and thus may be in an entirely different geographic location, or may be on the same premises. Further, the various manufacturing processes involving the garment manufacturing machine 112, the conductive inks 290 forming the electrodes 204, and the printer\dryer 104\108 may occur at totally different intervals of time and locations.

Machines that make garments such as but not limited to briefs, are often very large (e.g. about a city block long) and can produce garments at great speed, e.g. 1-500 units/minute. In an embodiment, the various features described herein are incorporated into a pre-existing garment manufacturing process, except that a pre-printed poly film (substrate) 212 (FIGS. 2A-2C) is further included. One advantage of such an arrangement is that using the pre-printed poly film substrate 212 described herein will not slow down the manufacturing process whatsoever.

Next, flexographic printing mechanisms are advantageous for low-cost print procedures. Flexographic printing mechanisms are suitable because they are fast, and flexographic printing presses usually have ample drying capacity tacked on to their back end. As such, flexographic printers can print and dry very quickly, so that the finished pre-printed poly film or substrate 212 can be rolled up and won't block (stick together or transfer print) being already dry. This is an important feature for the garment 200 in which management and detection of moisture is a consideration.

Flexographic printers are also often implemented in arrangements of multiple print-stations (e.g. printer $104_{1-n}$ and dryer $108_{1-n}$). However, the embodiments herein are not exclusively to multi-printer arrangements, nor are they limited solely to flexographic printing.

In an embodiment, the flexographic printer 104 prints an electrode 204 onto the poly film (substrate) 212, which is then referred to as a pre-printed poly film (substrate) 212. Afterwards, the dryer 108 performs drying on the combination. Upon being sufficiently dry, the pre-printed poly film (substrate) 212 may then be stored, either individually or in groups.

Further, in an embodiment, the pre-printed poly film (substrate) 212 may be (optionally) re-run through a single specialized (e.g. flexographic) printer 104 and dryer 108. Such a re-run or re-printing (over-printing) or double-printing would be at least for the purpose of assuring suitable levels of conductivity, specifically conductivity of the resulting electrode 204. A flowchart of such over-printing is shown within FIG. 8A.

Once the pre-printed poly film (substrate) 212 has completed its processes, including over-printing if suitable, then, either at that time, or (more likely) at a later time, and potentially in a different facility, the pre-printed poly film (substrate) 212 is fed into the garment manufacturing machine 112 as a pre-printed assembly. As part of that feeding process, the pre-printed poly film 212 can be, for example, located at a bottom of a garment 200, underneath the absorbent mass 220 as shown in FIG. 2A. A breathable outer layer 216 is the portion of the garment 200 which is positioned furthest from the human body.

An non-limiting example of a garment 200 is shown at least within FIGS. 2A and 2B. This arrangement is optimal to prevent the moisture, e.g. urine/feces from soaking thru to a bed, chair, or other surface. The pre-printed poly film (substrate) 212 does not get in the way of or cause any problems for the garment manufacturing machine 112 as the film (substrate) 212 is no thicker & no stiffer than the plain "poly" used in conventional garments. The embodiments shown in FIGS. 2A and 2B are for example only, and the embodiments herein should not be considered as limited thereto.

FIG. 2B illustrates what is meant by "continuous roll", where a roll of garments are shown separated by dashed lines. As the garments 200 are manufactured, the raw materials are combined in a continuous fashion. Most of the layers of the garments are initially on rolls, and they are introduced into the process at the appropriate time. The absorbent mass (filler) 220 is introduced into the manufacturing process in the form of "fluff" (raw fibers) which are later formed into various shapes which fit the human anatomy. This mass is laid down on the pre-printed poly film (substrate) 212, and then nonwoven layers are put below the substrate 212 in the garment 200, and then more nonwovens are put on top of the absorbent mass 220, to hold the absorbent mass 220 in place.

Next, various other cuts and adhesive tabs are added while the garment 200 is still in "roll" form, including various alterations to make the garment 200 fit human anatomy. The last manufacturing step for creating a properly layered garment 200 is cut to a pre-determined length and folded. This is important because the continuous strips of conductive ink (electrodes 204) are then completely encapsulated within the garment 200. At a top and bottom edge where the garment 200 is cut at the end of the manufacturing process, there is a thin nonwoven material on top of the electrode 204, the pre-printed poly film (substrate) 212, and perhaps (optionally) another nonwoven material underneath. This is the composite through which a conductive connection is made.

Within the embodiments of the garment 200 shown in e.g. FIG. 2B, the electrodes 204 are shown extending all the way to the edge of the substrate 212. However, this is for example only, for clarity and ease of illustration, but should not be considered limiting. It is not necessary that the electrodes 204 always be positioned this way.

Figure 2D:
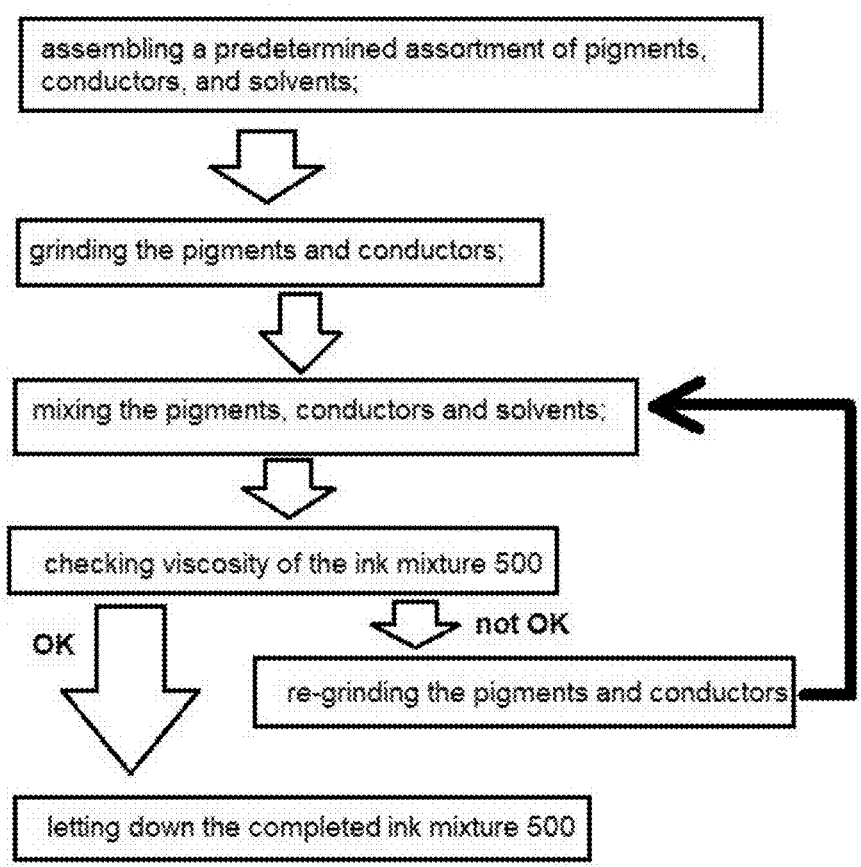
FIG. 2D shows an example method of manufacture.

The conductive inks 290 that form the electrodes 204 are printed onto a poly film (substrate) 212, which afterwards is referred to as a "pre-printed poly" film or substrate 212. These conductive inks 290 can be formed using a variety of methods, a non-limiting example being shown in FIG. 2D.

The materials in the conductive inks 290 can comprise metals, carbon compounds in various concentrations, graphite compounds in various concentrations, or any material that will conduct electricity in a dry or wetted condition. The conductive inks 290 may be used for various types of printing, paint, thread, or forming film made of various materials, etc. The conductive inks 290 may also be blended with non-conductors for deposition, storage, handling, and improved durability. An insulating layer may be used with the conductive materials. Hydrophilic and hydroscopic materials such as cellulose may be added to improve detection characteristics of the conductive element. Dissimilar materials may also be used to obtain a response different from those obtained from a single material type.

At some point, perhaps immediately, but more likely later, and perhaps in a different geographic location entirely, the pre-printed poly film (substrate) 212 is eventually included within a manufacturing process of a garment 200. The width of the pre-printed poly film or substrate 212 can be e.g. 40-50", but the embodiments herein are capable of printing multiple widths at once. As shown for example in FIGS. 2A-2B, the electrodes (AKA conductive strips) 204 are printed in a direction parallel to the movement of the garment through the printing machine direction, and set up to be continuous (uninterrupted).

The electrodes 204 may be ¼" wide and 2" apart, but this is an example only and should not be considered limiting. The pre-printed poly film 212 is trimmed to the exact width used in the garment 200, and is then delivered to the garment manufacturing machine 112. As such, the garment manufacturing machine 112 incorporates the pre-printed poly film 212 as a feeder component, similarly to how that machine 112 might incorporate the plain "poly" that is conventionally used in garment products.

In an example embodiment, the pre-printed poly film (substrate) 212 is configured to a predetermined width which conforms to a width within the garment 200 being manufactured. The garment-manufacturing machine 112 can use multiple widths simultaneously. In an embodiment, it is possible to arrange the electrodes 204 to be parallel to a direction of the garment-manufacturing machine 112, although this arrangement is not mandatory. The garment-manufacturing machine 112 continuously produces the garments 200.

As stated, FIG. 2B shows a parallel pattern that is integrated with a garment 200 in a continuous roll method. However, despite what is shown in FIG. 2B, alignment of the substrate 212 is not required to occur only along the direction of manufacture (direction of rolling).

The sensor elements (electrodes 204) are conductive elements which may have either a positive or negative response to moisture. For example, resistance of the electrodes 204 may increase when exposed to moisture, or may decrease. Both DC and AC measurements or other forms of applied voltage, including cyclic voltammetry, over both positive and negative voltages may be made to detect the presence of moisture or the properties and components of the moisture.

The electrodes 204 may be deposited onto the substrate 212 using one or more of rotogravure, flexographic printer (as mentioned), ink jet, offset, screen, extrusion, or xerography printing methods. The electrodes 204 may be made also be made of a material that is placed on, in, or through the substrate 212. Examples of the latter are conductive tape, thread, or wire.

Figure 3:
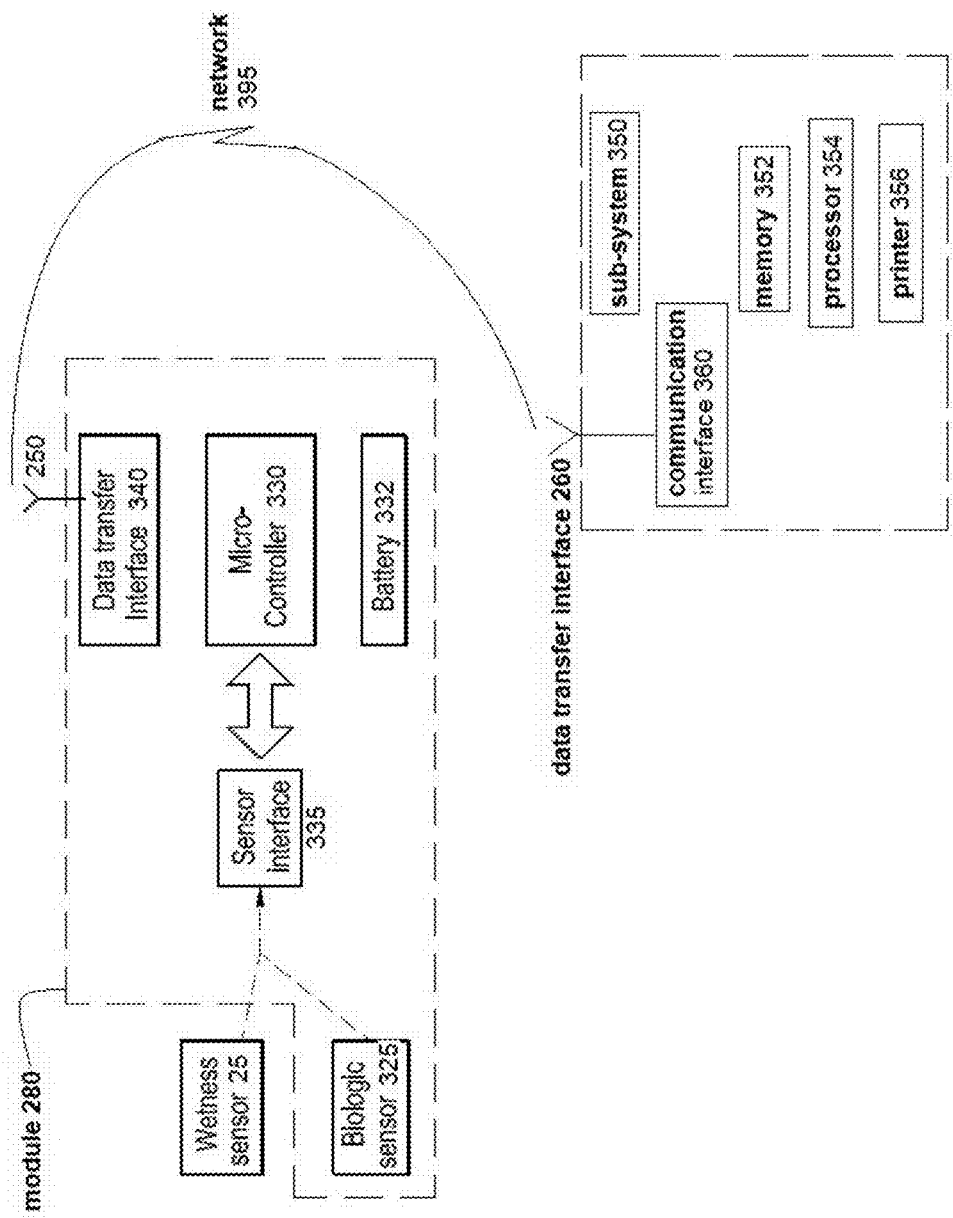
FIG. 3 shows detail of a sensor module.

FIG. 3 is a block diagram that incorporates some components of FIGS. 2A-2C in relation to other optional system components. The tag 200 communicates with either or both of wetness sensor 25 and biologic sensor 325, via a sensor interface within the tag. Signal transmission is also accomplished through microcontroller 330, which accepts sensor data indicative of the condition of a patient. Microcontroller 330 then relays such data to data transfer interface 340 which can be coupled to the antenna 250, for transmitting the signals to a separate data storage and processing sub-system 350 having an antenna 260 as well its own communications interface 360 for handling incoming and outgoing signals.

The module 280 can utilize any of a number of various communications protocols that have been described herein through either a wireless connection or wired means. In some embodiments, the sub-system 350 is equipped with memory 352, processor 354, and printer 356. Memory can be configured as either volatile or non-volatile memory, and includes in non-limiting fashion random-access memory (RAM), programmable read-only memory (PROM), flash memory, and other forms of database storage as well as any of a number of database management software tools for searching as would be typical for use with an electronic health record. Connection over the network 395 is optionally a public network using standard broadband transmission connected to various devices in multiple facilities and locations. Alternatively, network 395 is a private network of devices and clients linked over a local area network over a dedicated network connection.

In an embodiment, the processor 354 can be used for interpreting, sorting, and aggregating the received data. For example, machine-readable program instructions stored on processor 354 may be configured to interpret a "1" value to represent a wet or soiled brief, while a "0" value is interpreted to represent that no void event has occurred since a most recent changing. Each tag 200 has a unique identifier that enables the system to associate the information to the particular patient with that tag.

Figure 4A:
FIG. 4A shows a first of a plurality of mobile GUIs used within the embodiments herein.
Figure 4B:
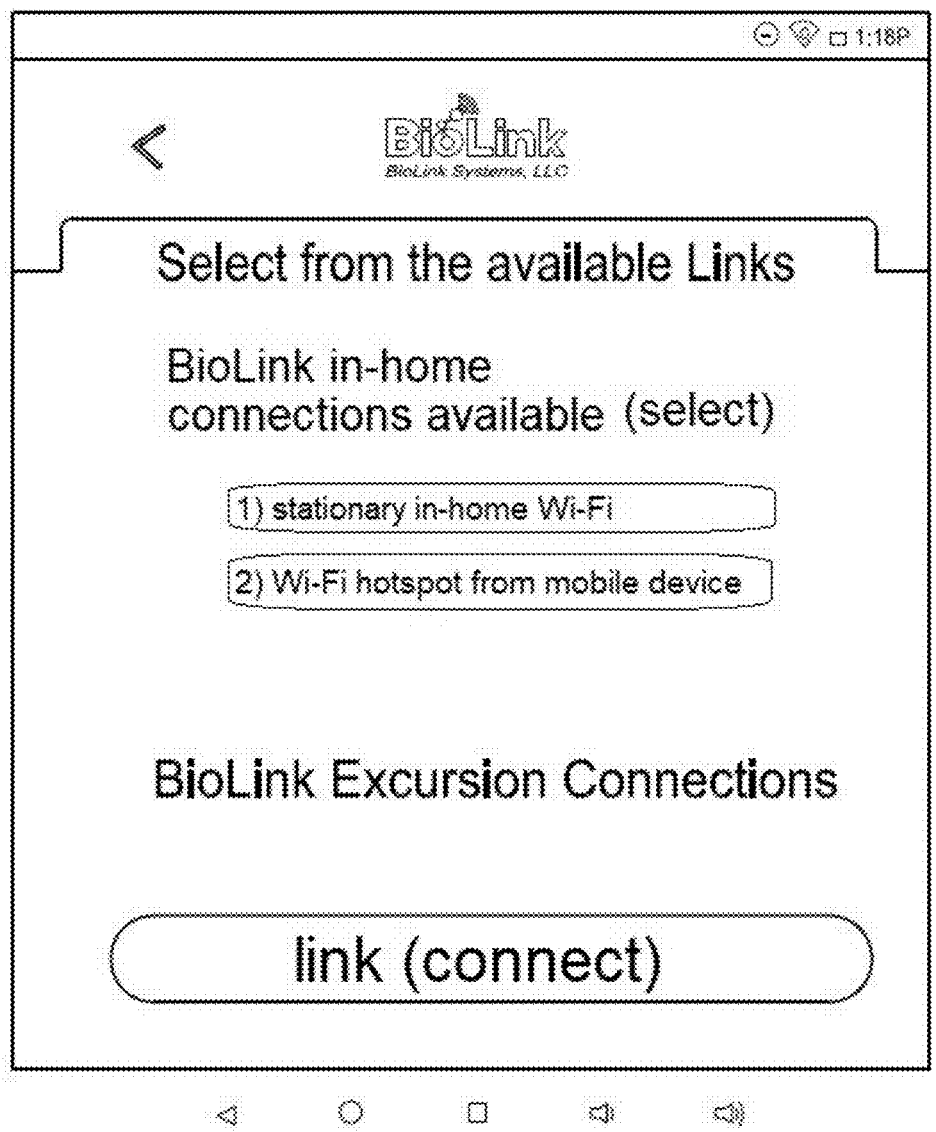
FIG. 4B shows a second of a plurality of mobile GUIs used within the embodiments herein.
Figure 4C:
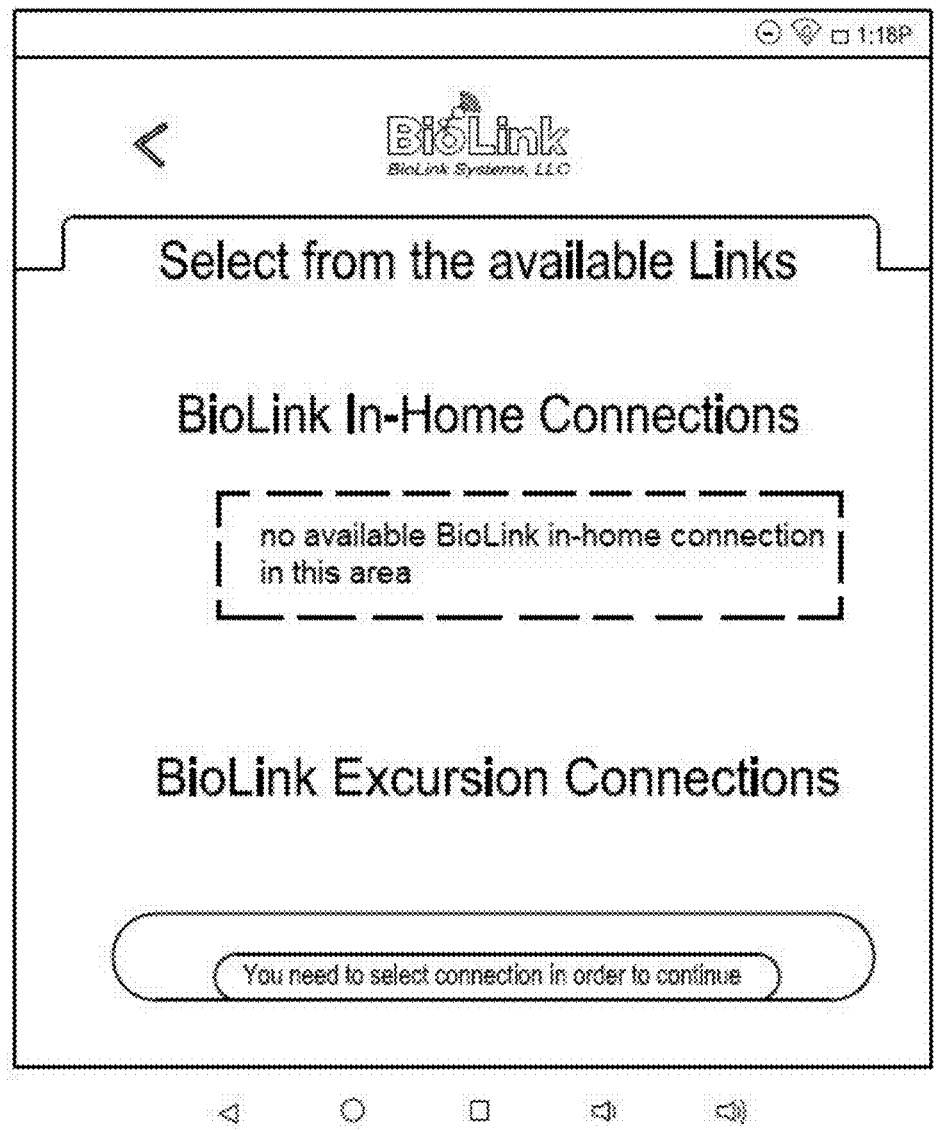
FIGS. 4C-4D show third and fourth of a plurality of mobile GUIs used within the embodiments herein.
Figure 4D:
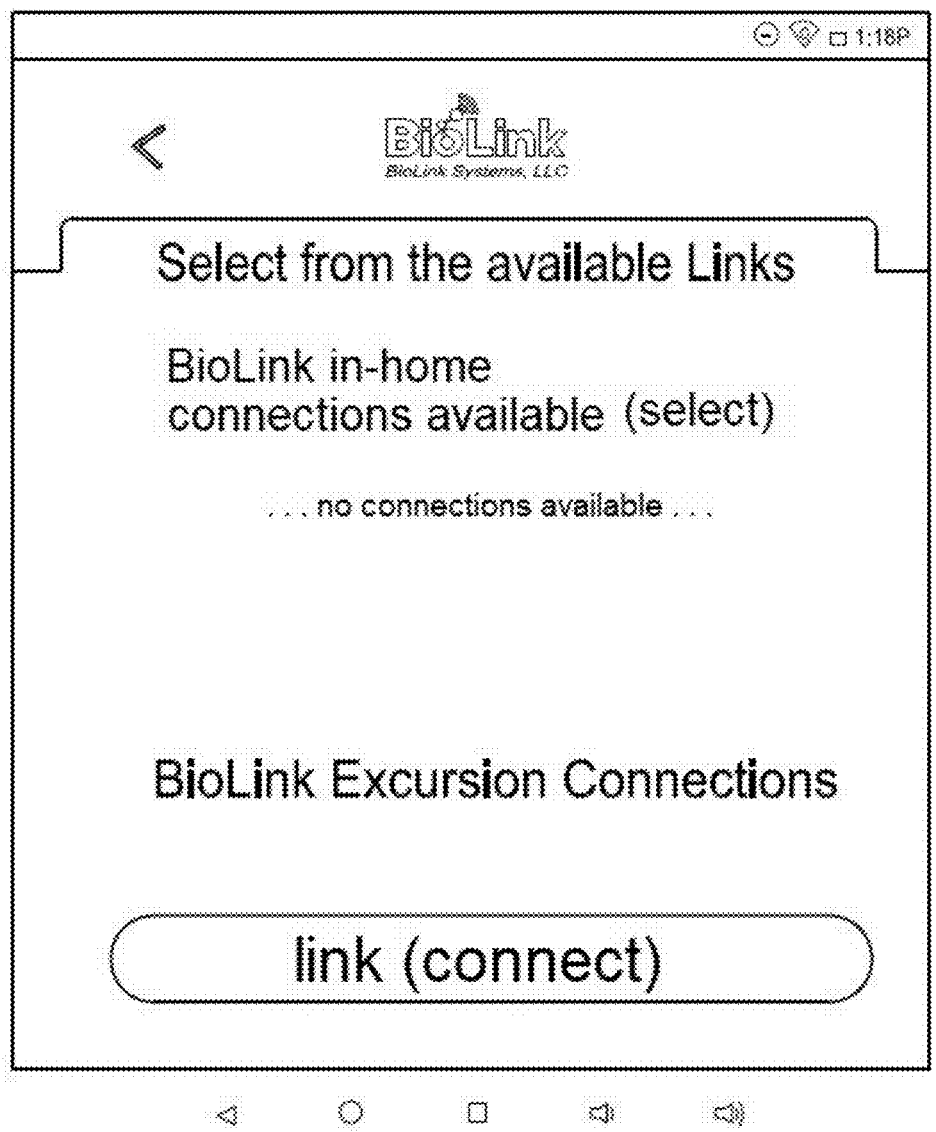

FIGS. 4A-4D show example non-limiting GUIs (Graphical User Interface) within an example mobile app, generally used for in-home non-institutional purposes. The bio-information sent to the GUIs shown in FIGS. 4A-4C comes from the module 280 (FIG. 2C). FIG. 4A shows an introductory screen, and FIG. 4B shows how a user will be advanced to selecting some type of in-home computer network location, two examples of which are "stationary in-home Wi-Fi" and "Wi-Fi hotspot from a mobile device". Thus, within FIG. 4B, the "locations" are not physical locations but network locations. Users can only connect to one location at a time. FIG. 4C shows an example message that comes up when a user has not selected any network. FIG. 4D shows an example GUI showing an instance where no computer-network locations are available.

In an embodiment, the processing sub-system 350 can be a type of caregiver workstation such as is typically used in a nursing home or residential facility. However, the data transfer interface 340 can also be contained in a mobile device such as what is shown in FIGS. 4A, 4B, 4C, and 4D.

Figure 4E:
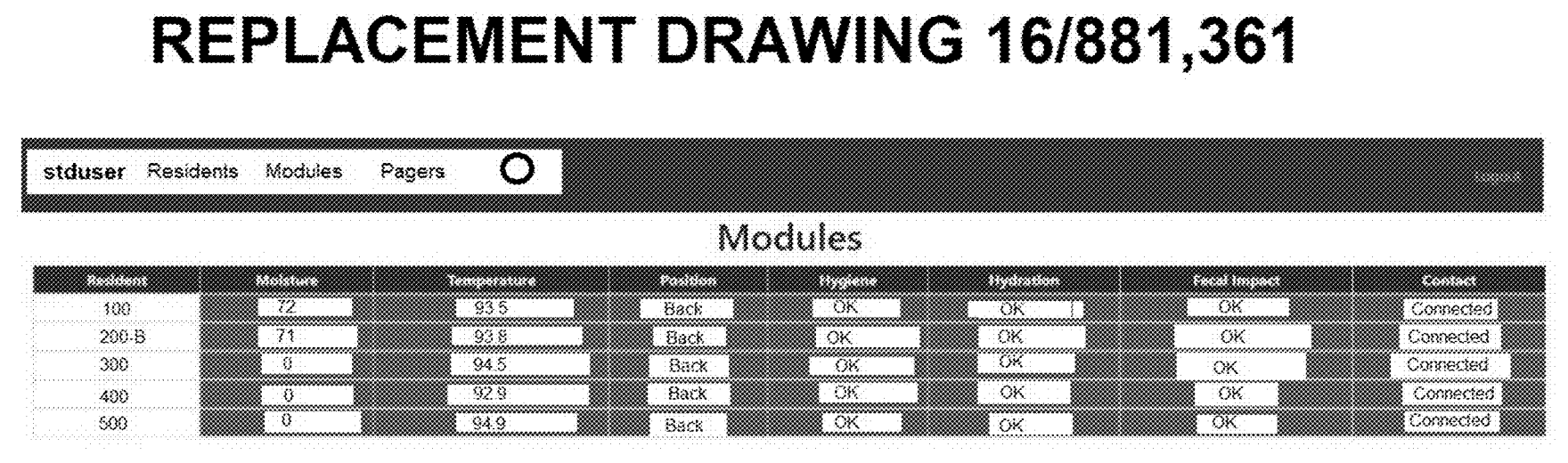

Again, the embodiments herein serve both at-home non-professional caregivers (e.g. relatives) as well as professional caregivers in e.g. hospitals, nursing homes, and other institutions. Accordingly, FIG. 4E shows a GUI for software used by a non-home fully professional environment, such as a nursing home, hospital, or other type of institution. In an embodiment, the processing sub-system 350 works with the GUI used by a non-home fully professional environment shown in FIG. 4E.

The substrate 212 can be a paper, fiber, a plastic film, or other material that can form a 'fil' (not a spelling error) of mesh. The substrate 212 can be smooth, or contain embossed features to improve deposition of materials. Embossing or patterning of the substrate 212 can be used to improve resistance to broken conductive paths of the electrode 204. Other alterations to the substrate 212 can also include corona treatments. However, in the event such alterations are included in the substrate 212, the printing service-provider (likely to be different than the manufacturer of the ink mixture 290) needs to be apprised of such changes to the substrate 212, as that printing service-provider may need flexibility to make changes to their version of the ink mixture 290, as well as to their print-heads and mechanisms applying the ink mixture 290.

Optionally, tracked information such as that shown in FIG. 4E (and elsewhere) is aggregated and further processed to provide patient-specific information on average interval between voids, for example based upon the last ten (10) such events, or any suitable sample size as desired. This can prove helpful in predicting future events or establishing a pattern of knowing when to look for the next such event. Though not shown in FIG. 4E, other information tracked and listed may include the current status of the patient: whether "dry" (no voids since most recent changing), or "wetness detected," including an indication of the duration since this finding occurred. There are various ways to depict the status as can be chosen by the user, for example as visual piece of information or an icon with a bubble darkened next to one of several optional levels to indicate the status.

Where the GUIs of FIGS. 4B and 4C say "Excursion mode", that refers to a Bluetooth connection to a mobile device 280. In that embodiment, the module 280 and the mobile device or tablet (and displayed by the GUIs) are the only hardware. The module 280 advertises via Bluetooth and the mobile device or tablet picks up that advertisement if within range. Simplicity is the advantage here, but the limited range of BlueTooth® (e.g. 30 feet) can be somewhat of a disadvantage. Thus, the "excursion" of FIGS. 4B and 4C can be a distant excursion, but the distance between the module 280 and whichever type of mobile device should not exceed 30 feet (BlueTooth range). The word "excursion" arises from the idea of a relative or loved one taking a resident away from home or out of a nursing home or other facility for e.g. a mini-vacation, e.g. excursion.

Figure 8A:
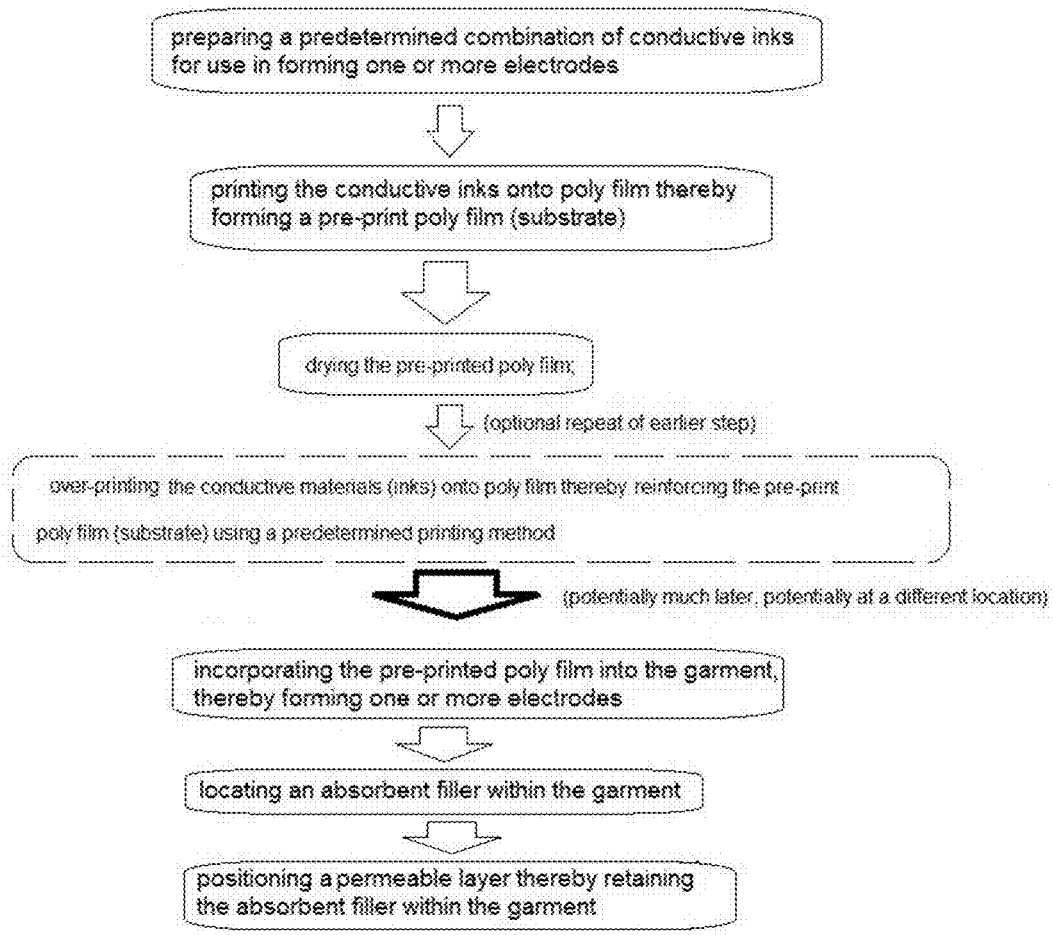
FIG. 8A is a flowchart showing a method of manufacturing the embodiments.
Figure 8B:
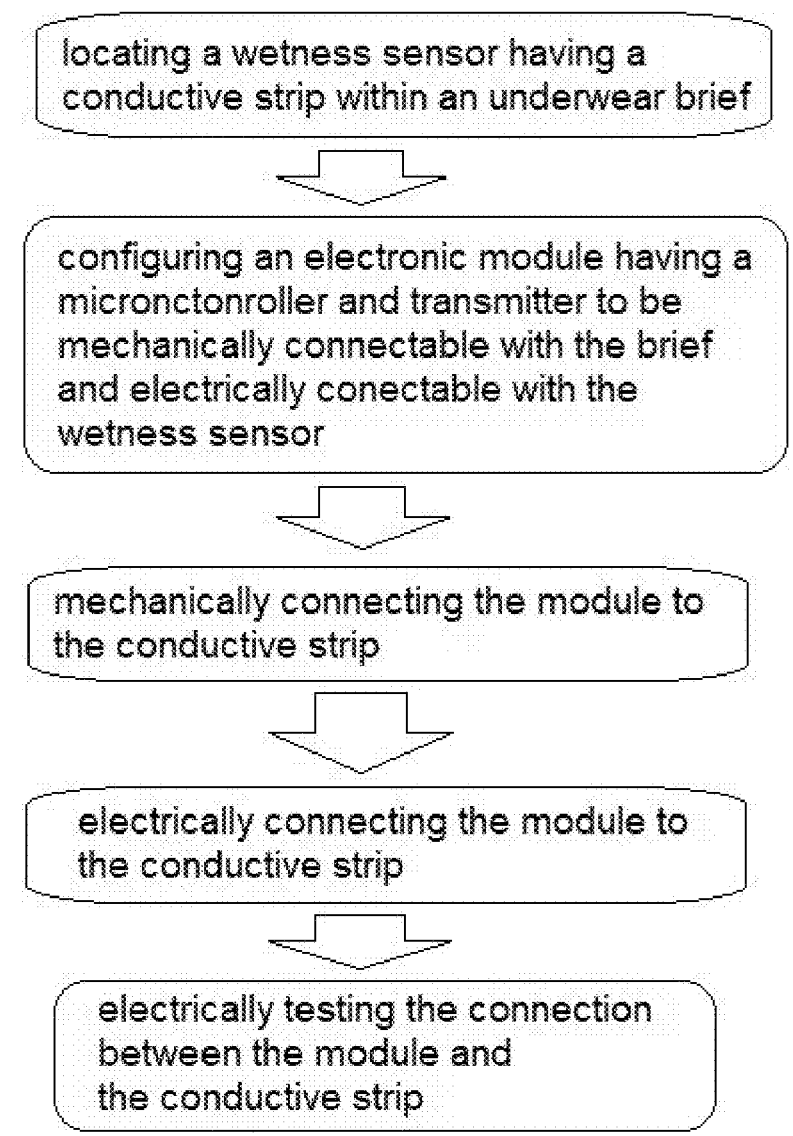
FIG. 8B is a flowchart showing a method of testing the embodiments.

FIGS. 8A and 8B show flowcharts of a method of assembling and testing a garment 200. Regardless of the specific form of the resulting garment 200, all embodiments discussed herein will be manufactured using some variation of one or more electrodes 204 in the form of conductive strips. All embodiments discussed herein will be disposable. In other words, it is intended that there will be no laundering of the garment 200. Whether the garment 200 is in the incontinence diaper format or the briefs (underwear) format, the garment 200 will be single-use, disposable, and not intended to be laundered or re-used.

Another advantage of the embodiments herein is that it is possible, in some embodiments, to reduce the thickness of the absorbent filler 220. In some existing garments, the amount of absorbent filler is sometimes increased in order to minimize discomfort on the wearer if their diaper remains unchanged for a while. In contrast, the embodiments herein overcome this because when the embodiments herein are properly implemented, the active, real-time monitoring for wetness that occurs will limit how long a person will have to wear a wet garment/diaper, so that extra filler 220 is un-necessary. This in turn can reduce the cost of the garment 200.

In an embodiment, moisture within the garment 200 is sensed by measuring the resistance between two conductive paths. When moisture is present between these paths, the resistance can, for example, increase or decrease. The value of resistance can be, for example, a function of the sheet resistance of the parallel electrodes 204, the distance from the measurement connection of the module 280 to the moisture, the conductivity of the moisture applied across the conducting paths, and for some material, the voltage applied to measure the resistance.

FIG. 9 shows a flowchart of an example method of using and operating the garment 200. Although they are preferably reusable, it is anticipated that modules 280 will need to be replaced eventually. Also, it is possible for modules 280 to become lost or misplaced. Thus, it will often be useful to track the status of the module 280 itself. In some embodiments, this is accomplished by recording the date a module 280 was first put into use and otherwise implemented. This is accomplished by assigning a unique identifier to a particular module 280 such as but not limited to a MAC address. From that point, all data associated with that identifier is linked to the particular module 280.

A typical life cycle of a module 280 can be determined and used for calculating and showing how many days until replacement will be needed. It is also possible to track information such as the length of time since the battery was last changed or replaced. The modules 280 can also be equipped with a function capable of responding to a query sent via Bluetooth, programmed to be directed to a specific module 280 based on its identifier, in which the module 280 associated with the identifier emits an audible noise in response to the query.

Begin Network Topography, Including Role of Access Points 504

Figure 5B:
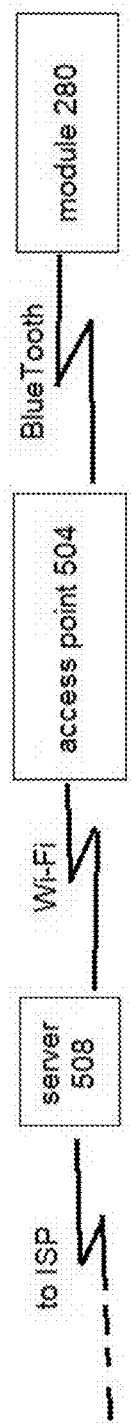

As shown in FIGS. 5A and 5B, a system 500 comprises a plurality of access points 504 which receive the resident data and send the data to the server 508. The information for each resident is transmitted over Bluetooth approximately every e.g. 3 seconds, although this time-interval can be adjusted. The server 508 analyzes the data and continually updates a database 512 with the current resident information. A web interface 520 displays the information that it reads from the database 512. In an embodiment, the web interface 520 can be similar to a web browser interface, but the embodiments herein should not be considered as limited thereto.

During normal operation, the server 508 will increment a value in the database 512 every few seconds. The web interface monitors 520 this value to verify that the server 508 is operating correctly. The status of the server 508 is displayed as a Green dot on the status bar, an example of which is shown in FIG. 7C. Currently, if the web interface does not detect any change in the value, then there may be an issue with the operation of the server 508, so the dot turns Red.

As stated, the module 280 transmits biometric data at predetermined intervals, e.g. every 3 seconds. These modules 280 are battery operating and may fail due to e.g. the battery. While powered on, the module 280 will continue to send biometric data to the server 508. The server 508 maintains a timestamp of the last time data was received from that module. If a set amount of time elapses without receiving data from a module 280, the server 508 marks that module 280 as 'Inactive', and can potentially also send an alert or a page.

The modules 280 are automatically added to the system 500 when the data from the module is delivered to the server 508 for the first time. A module 280 will remain in the system 500 until an administrator manually removes it.

The web interface 520 indicates the loss of a specific, i.e. errant module 280 by displaying the module data as 'Grayed Out', as shown in FIG. 7D.

The cause of data not reaching the server 508 may be due to a failed access point 504, which delivers the data to the server 508, but this is not likely. Each module's BlueTooth advertisement is received by a number of access points 504 in the system 500, and thus would be expected to be reported by two or more of the various access points $504_{1-n}$. This redundancy can be achieved at low cost and low power consumption, as access points 504 are architected to be inexpensive, replaceable, and work well in groups. Thus, the access points $504_{1-n}$ form a type of mesh network 590 (FIG. 5C).

Figure 7A:
Figure 7B:
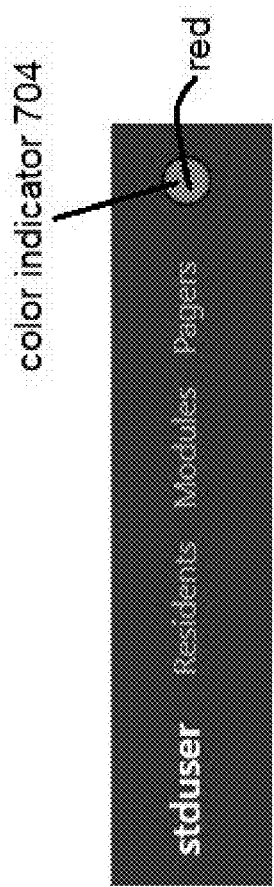
Figure 7C:
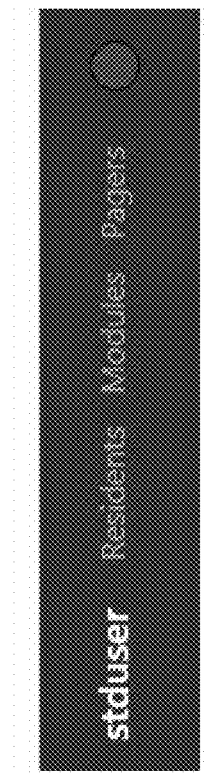

A GUI of a functioning, stable access point 704 is shown in FIG. 7A. For contrast, a GUI of a failed access point 704 is shown in FIG. 7B, in which a color indicator 704 is switched to red.

The access point 504 delivers biometric data received from the modules 280 to the server 508 for processing, such delivery being via the numerous BlueTooth advertisements from the modules $280_{1-n}$. The server 508 will automatically add a new access point 504 to the system when it first connects to the server 508. Like the modules 280, the various access points $504_{1-n}$ will remain in the system 500 until manually deleted by an administrator.

The server 508 continually maintains a list of all of the attached access points 504 and marks those access points as 'Active'. As shown at least within FIG. 7A, a list of all access points $504_{1-n}$ and their current state can be viewed by a user with administrator rights from the access point page (not shown) of the web interface 520. If a known system access point 504 is not connected to the server 508, the state of that access point 504 is marked as 'Inactive'. The web interface 520 displays a GUI with an 'Inactive' access point 504 being grayed out.

As shown in FIG. 5A, the access points 504 are located in various places that will pick up BlueTooth advertisements from the modules 280. The access points 504 pick up the information, extracts the data out of the broadcast, connect to the server 508 over Wi-Fi network, and pass the information to a server 508, which in an embodiment may be a Linux server.

The access points 504 sit and listen to all modules 280 within their range, and as shown in FIGS. 5A and 5C are installed and intentionally spaced to always have multiple access points 504 receiving signals from any given module 280. There are some thresholds at the signals (BlueTooth advertisements) in that some signals may be discarded, because other access points 504 will detect the same signals. So, when the server 508 gets signals from all the various access points 504, there may be duplicate information. The server 508 has the ability to sort and discard duplicate signals. The result is the redundant network or mesh network 590 can be adjusted and re-configured according to conditions. Further, the access points 504 can be disconnected and moved depending on load, usage, signal blockage, and changes in the numbers of residents.

Within this disclosure, the expression "advertisement" refers to Bluetooth. The expression "broadcast" may refer to either BlueTooth or Wi-Fi. While a Bluetooth advertisement is like a broadcast, a person of ordinary skill would recognize the BlueTooth communications are more often referred to as advertisements and not as broadcasts.

Next, anybody can see the information in a Bluetooth advertisement. There is no attempt to disguise or encrypt the BlueTooth advertisements. This is advantageous because any access point 504 can pick up any BlueTooth advertisement from any module 280, so that such redundancy increases reliability of the mesh network 590. Further, because the BlueTooth advertisements do not contain data of which a breach would be a Health Insurance Portability and Accountability Act (HIPAA) violation, it is not possible to trigger a security breach occurring through intercepting the BlueTooth advertisements. As such, the access points 504 can pick off the advertised data and re-connect to the server 508 making a point to point connection.

The access points 504 are plugged into wall outlets and thus always under power, and thus don't need to be re-charged. The access points 504 track the advertisements, extract the data, and send that data to the server 508 which in an embodiment can be running e.g. Linux. The server 508 accepts incoming data, takes out any duplicate entries, and then makes an entry into the SQL database 512. In doing device-discovery, the server 508 listens to everybody who has broadcasted, and then reports the various access points $504_{1-n}$ who are broadcasting to the server 508. This process continually affirms which access points 504 devices are on-air and properly connected.

Begin Discussion of Software GUIs

As discussed previously with respect to FIGS. 5A and 5B, the embodiments herein include a patient management system 500 accessible by various software GUIs (e.g. FIGS. 6A-6E and 7A-7D) which will be described as follows. A login screen (not shown) will be the first page that appears when starting the web application 520. There will be two text boxes on the screen below the navigation bar. The first box is for the staff member's username. The other box is reserved for the user's password. Both boxes must be filled in for the user to continue to the web application 520. Leaving either box blank will present the user with a warning message informing that the user must fill out both fields. A warning will also appear if the user doesn't exist or if the incorrect password for that user is entered. When the correct user credentials are entered, and the "Log In" button is clicked, the user will be logged in and sent to the GUIs shown in FIG. 6A (standard user) and 6B (supervisor).

Depending on which type of user, the "Modules" portion of the GUI will have different looks to it. For example, as shown in FIG. 6B, the administrators and supervisors will have the ability to remove modules, where the standard users (FIG. 6A) will not. As shown in FIG. 6A, on the standard user's module portion, the MAC addresses of the modules 280 will be hidden. Within the GUI 604 shown in FIG. 6A, users can view the statistics and vitals of the residents associated with the various modules 280. The information displayed on the GUIs of FIGS. 6A and 6B will be updated every 20 seconds, or may be forced to update by pressing the "reload" button of the browser.

As shown in FIG. 6B, within in the GUI 608, the Administrator and Supervisor will see additional information that is not pertinent to a standard user, including the modules 280. However, all users will see that status information that is monitored by the system 500. The display will show all residents in a table format and the user may have to scroll down to view patient information that may not fit on a particular screen.

In FIG. 6B, the MAC Address column 620 displays the MAC (Media Access Control) address of the module 280 that is supplying the data that is displayed for the specific resident. Each module 280 will have its own MAC address. As described with respect to FIGS. 5A and 5B, data is received from the module 280 via Bluetooth. Accordingly, the MAC field displayed in FIG. 6B is a Bluetooth address of a particular transmitting module 280. As stated, this MAC field is only used to uniquely identify the module 280 and is only visible to Supervisors and Administrators.

The Resident column (FIGS. 6A and 6B) displays the Resident Identifier associated with the BioLink module 280 indicated in the MAC address. The identifier used will depend on the system setup, preferences of the specific facility, etc. In an embodiment, this column may display e.g. a name, room number, internal identification value or other.

The Moisture column (FIGS. 6A and 6B) displays the current moisture content of the residents brief, ideally in a percentage format, i.e. ranging from 0-100%. The moisture value is used to help indicate when a resident has a soiled brief. The expression "help" indicate is important, as there are many different factors in determining whether a resident is truly "wet" or not. The module 280 and garment 200 provide accurate, reliable information, but are not infallible.

The Temperature column (FIGS. 6A and 6B) displays the current temperature of the patient.

The Position column (FIGS. 6A and 6B) display the current position of the resident based on the orientation of the module that is attached to the garment 200. Some example values that may be displayed in this column are back, stomach, left side, right side, standing, and invalid (does not correspond with any known value, possible transmission or signal error, or when the module indicates that the resident may be, for example, standing on their head). A Position alarm will occur when a resident has remained in a single position for a timeframe longer then a value programmed for that resident. This alarm is automatically cleared when the resident moves or is moved to a new position.

At this time, a clarification is needed. Within this disclosure, the words "alarm" and "alert" are sometimes used in very similar ways. An alarm is not an alert, and an alert is not an alarm. An alarm is a condition, while an alert is a possible event resulting from that condition. Alarms typically happen at the resident side, while alerts are sent to caregivers based on triggering of an alarm. Thus, alarms are patient-side, and alerts are sent to the caregiver side of things. In other words, within this disclosure, an alarm is a state of existence, while an alert is an event.

The Hygiene column (FIGS. 6A and 6B) displays the state of a Hygiene Alert feature. A Hygiene alarm is issued when the time to clear a moisture alarm is less than a time programmed in the system for that resident. A Hygiene Alert is a warning that the cleanup of a resident's soiled brief may not be adequate. The system has a programmed interval for each resident that define the amount of time that cleanup is expected to take. This value is based on a number of factors which includes the mobility and physical stature of the resident. This value may or may not differentiate the cleanup of urine vs bowel movement, and is a subjective value. The system 500 facilitates extensive configurability and customization of these values according a variety of facility-specific factors.

The Hydration column (FIGS. 6A and 6B) displays the state of the Hydration Alert, meaning how long since a resident had a drink. A Hydration alert occurs when the amount of time programmed for a resident elapses and the resident has not generated a Moisture Alert. This may be an indication of a dehydration condition e.g. the resident needs a drink or needs their IV reviewed. The alert will automatically be cleared on the next Moisture alarm.

The system 100 maintains information per resident on the occurrences of moisture alerts. A Moisture alert indicates that the resident has a soiled brief from either urine or a bowel movement. The system 500 is programmed, per resident, with the expected time between moisture alerts. If the programmed time elapses without a moisture alert for the resident, then this will alert the staff about the possible dehydration of the resident.

The Fecal Impact column (FIGS. 6A and 6B) displays the state of the Fecal Impact Alert. The system maintains information per resident on the occurrences of Moisture Alerts. The Moisture alert indicates that the resident has a soiled brief from either urine or a bowel movement. The system is programmed, per resident, with the expected time between moisture alarms due to bowel movements. If the programmed time elapses without a moisture alarm due to a bowel movement for the resident, then this will alert the staff about the possible bowel impaction condition of the resident.

A Hydration alert occurs when the amount of time programmed for a resident elapses and the resident has not generated a Moisture Alert. This may be an indication of a dehydration condition. The alert will automatically be cleared on the next Moisture alarm. A Fecal Impact alert occurs when the amount of time programmed for a resident elapses and the resident has not generated a Moisture Alert due to a bowel movement. This may be an indication of an impaction condition. The alert will automatically be cleared on the next Moisture alert caused by a bowel movement.

The Contact column (FIGS. 6A and 6B) displays the state of the connection of the module 280 to the garment 200. In an embodiment, the status will display 'OK', 'Ajar' or 'Disconnected', although other states may also occur. In an embodiment, the module 280 attaches to the garment 200 by e.g. two or more conical-shaped teeth, where these conical teeth make both mechanical and electrical contact. If any of the conical teeth are not firmly connected to the brief then the system will display an 'Ajar' alert. If the module is totally disconnected from the brief, the system will display 'Disconnected'.

The "modify" column allows a supervisor or administrator to delete a module 280 from the system.

An alarm is a condition where a measured value is outside the expected range or beyond a defined threshold. When an alarm condition arises, the parameter that is in the alarm state will turn Red and a page or other signal (e.g. alert) to a staff member may be issued. The actions taken in an alarm state will depend on the system configuration of the facility.

Depending on the type of condition, specific action may be required to clear the alert. In general, when an alert condition arises, the alert will be indicates by displaying the screen item in red (e.g. FIG. 7B). As mentioned, depending on the setup of the system, a page may be issued to staff member to address the alert. The system may be programmed to issue reminder pages, if the alert exists longer than a programmed amount of time. In some instances, it may not be possible to clear the alarm within the time that has been programmed to dispatch a reminder page. In this instance, the alarm may be 'acknowledged' via the web page to disable further paging for the alert. Note, this feature will not clear the alert, but simply disable the reminder pages.

Figure 6E:

A Temperature alarm occurs when the resident's temperature falls below or rises above an adjustable, predetermined level. This alarm will automatically clear when the temperature returns to expected levels. The following shows how a Temperature Alarm would be displayed. The GUI in FIG. 6C displays the current temperature and beside the alarm also indicates the number of minutes that the alarm has been active. In an embodiment, the Temperature value also provides a hyperlink to a page that is used to acknowledge the alarm. As shown in FIG. 6D, when hovering over the value in alarm, the value will be underlined to indicate that it is a hyperlink. When the hyperlink is pressed, the system will redirect to the page as shown in FIG. 6E, which gives the user an opportunity to acknowledge the temperature alert.

Once the alarm has been acknowledged, any future Reminder pages will be canceled. The act of acknowledgement will also remove the hyperlink from the value, since it can't be acknowledged again. Meanwhile, the temp value will remain in an "alarm" state until that value returns to an expected level.

Moving away from temperature toward wetness, a moisture alarm occurs when the percent moisture of a residents brief exceeds the programmed limit of the resident, or some other type of pre-set limit, perhaps not a percentage but some other type of metric. The alarm condition will remain until the resident is cleaned up and the garment 200 replaced. During servicing of the alarm, it is extremely important that the specific cause of the moisture alarm be indicated using the buttons that are present on the module 280. This alarm is automatically cleared when resident has been cleaned up and the garment 200 has been replaced.

A Disconnect alert (FIGS. 6A and 6B) occurs when the attachment of the module 280 to the garment 200 is not complete, perhaps due to coming loose, either mechanically or electrically. This alert is automatically cleared when proper attachment of the module 280 is restored.

The information displayed in the Residents column contains a hyperlink to a page that displays a 'View Only' form of the resident selected. This GUI will show the specific values programmed for a resident, but only in read-only format where no changes can be made. Modification to the resident information must be made from the Residents column by a user authorized to make system changes.

The Resident column is used to list all residents currently programmed into the system. If the user us a Standard User, then this page is 'View Only'. For administrators, this page allows users to be added, and also allows a specific module 280 to be assigned to a specific resident.

A Pagers GUI (not shown) lists all of the pagers that have been assigned in the system. If the user is a Standard User, then this page is 'View Only'. For administrators, this GUI allows pagers to be added and assigned to residents. In an embodiment, a single pager can be associated with a number of residents.

As shown in TABLE 1 below, a pager is also assigned to a class, or Nurse Role. In an embodiment, the supported classes are Charge Nurse (sometimes referred to as a "duty nurse") or Certified Nurse's Assistant (CNA), although other classes could be added, so that this list is non-limiting. CNA's are sometimes referred to as Nurse's Aides.

The alerts are configured to possibly notify a specific class of worker based on the type of alert. The following table shows which alerts are sent to which class of pager.

| ALERT TYPE | NURSE ROLE |
| --- | --- |
| Turn | Charge Nurse and CNA |
| Disconnect | CNA |
| Moisture | CNA |
| Hygiene | Charge Nurse |
| Hydration | Charge Nurse |
| Hydration | Charge Nurse |
| Fecal Impact | Charge Nurse |

Table 1: Types of Alerts v. Nurse Roles

The system 500 is composed of a number of components. The web application 520 can be used to flag ant notify that there may be a problem with the system 500. Since system issues will typically involve administrative users (supervisor) only, there are limited indications to the standard user.

This completes the explanation of various of the GUI's herein.

All access points 504 are assigned a fixed IP address by the server 508 when those access points 504 power up. That is, at power up, the access points 504 make a TCP/IP connection to the server 508, which puts an entry into the SQL database 512, which occurs entirely in the background so there's no human interaction required.

As shown in FIG. 5A, the web-based application 520 runs on the server 508. In an embodiment, the web-based application 520 can be viewed using a cloud-based application such as but not limited to Azure.

If a user is looking through cloud files using e.g. Azure, one could achieve that doing an Amazon Web Services (AWS) or Azure inquiry. Conversely, if just doing using just a local network inquiry, these would be only viewable by persons within that nursing home facility or within a connected network, e.g. some type of corporate mechanism. If a user wants to monitor from home, they have 2 options: either provide a VPN connection into an office so that a remote home PC looks like it's at the office, or put the data on a cloud. If on the cloud then anybody can see it. If the data is on the cloud, one could use a mobile device and see that data on mobile phone, tablet, or PC.

The Unix, Azure, or AWS user would likely not be a nurse. Instead, this would be a person evaluating e.g. facility-level data, and not so much resident-level data. Also, in an embodiment, a cloud-based system could entirely replace the server 508.

Global Data Aggregation (e.g. Tracking Whole Facilities, not Just Residents)

The modules 280 sends their data via continuous advertisements, so the access points 504 pick out the advertised data and forward the information (if changed) to the server 508. As such, the embodiments herein have a high degree of repetition of tasks. However, this in turn produces a high volume of data, some redundant, which can be curated and managed by interested parties, and is thus of significant value.

In contrast to the embodiments herein, existing (Prior Art) facilities may perform some data-gathering, but they do so largely manually. In such a manual system, some residents may not be looked at for 4 or 5 hours and even such a "look" may not include their diaper. In sharp contrast, the embodiments herein know exactly what is occurring in every garment 200 every minute of every day (actually every 3 seconds). This feature offers game-changing advantages to a purchaser of the embodiments herein.

In an embodiment, it is possible to organize the group-data by facility, or by groups of facilities, or by corporation, so an owner or executive e.g. management can spot whether one facility is going badly, or whether this is a trend this that's across a certain type of facility, or access the whole corporation. An ownership entity can combine multiple facilities in some way to view all that information. In an embodiment, each facility has its own database 512. However, it is possible for a customized application to connect to all the databases and merge portions of the data.

One advantage of the system 500 is always knowing exactly what is occurring inside of any patient's diaper. Statistically, the system 500 gives management the ability to understand what is going on within every garment 200 in the entire facility, all at once. Such scalability is advantageous.

The system 500 changes many aspects of nursing home workflow and behavior. In a conventional facility, when a Nurse's Aide reports for work at 6:00 o'clock in the morning, it may be necessary to check 20 briefs or 30 briefs to see who's wet. Meanwhile, using the embodiments herein, that Nurse's Aide could go directly to the exact/only 3 briefs that are known to be wet. There is a big increase in productivity when checking 3 particular units of anything, as opposed to 20-30 of anything.

A embodiment also discloses a radio frequency pager or a standard pager that can have messages like "XYZZ pulse rate below 40, suggesting coma". This feature helps in detecting and resolving emergency situations.

As stated, it is also possible to extrapolate all this information out to corporate information or to regional information and view that information using e.g. Azure. This is important for managing numerous different facilities, including making determinations about which facilities are run well, and which are run poorly.

The system 500 can also be adapted to patient conditions and circumstances. Some facilities have patients that are there for custodial purposes and other facilities have residents that are present because they are sick or infirm. The embodiments herein are sufficiently configurable that they could adapt to either situation, or others.

To re-phrase slightly, a large amount of data will be collected as a part of the testing and ongoing utilization of the system 500. This data will be "new" data as relates to bowel and bladder functioning in the nursing population. This data will be relatable to outcomes such as UTIs, bowel impactions, other types of medical problems which plague nursing homes and residential facilities. Such data could be clinically very important to future use of the system 500. Further, various embodiments of the system 500 will have data scientists honing, fine-tuning, and extracting value from the large volume of data made available, that is not available without with system 500.

Hardware of Access Point 504

In an embodiment, the access point 504 can be a Raspberry Pi. There are other hardware platforms that are low cost, of which "espress IF" is just one example. The hardware forming the access point 504 needs BlueTooth and Wi-Fi capability in the same box, and it will be helpful although not required to have the access point 504 run the Linux operating system. As stated, one alternative could be "espress IF". Further, the company ST Microelectronics also has various models of development boards having Wi-Fi capability.

A Raspberry Pi may not be perfect for a production product because it's really not made for permanent end-use, although it can achieve that. Instead, Raspberry Pi is an experimental board to achieve proof of concept. For example, some Raspberry Pi's have difficulty with power conditioning. Further, with older Raspberry Pi hardware, if a sudden power loss occurs, can corrupt the SD card which is a memory card so all the memory and everything on that board gets corrupted. If this occurs, the result is the whole raspberry pi device may not work. Conversely, a proprietary special-purpose board could have the boot-code as flash ROM, thereby never losing any code regardless of power conditions. Or, a hybrid-modified raspberry pi with improved power-conditioning and other ruggedizing factors could be implemented.

Physical Facility Issues

Both BlueTooth and Wi-Fi signals can be obstructed by walls or other issues, thereby causing networking problem of the access point 504. There's number of other factors, e.g. building construction, that can also impede signal. To address this, multiple access points 504 form the mesh network 590, as shown at least within in FIG. 5C. Further, the spacing of the access points 504 with respect to the module 280 is set up such that any module 280 should always reach multiple access points 504. This redundancy should overcome problems in facilities (e.g. thick walls, antiquated structure, poorly wired, etc).

If the building structure are signal-resistant, the embodiments herein e.g. the mesh network 590 might be able to route signal through some other type of connection, e.g. some wired network, repeaters, or other type of way of getting information to the server 508. In any event, all communication is wireless, using of any kind of nursing home network, and can use Wi-Fi repeaters to traverse long hallway or changes in altitude. Both Wi-Fi and BlueTooth are known to be impeded by wall-blocking, but the mesh network 590 should solve the BlueTooth side of this, and (if necessary) Wi-Fi repeaters can solve problems on the Wi-Fi side.

Another good thing about the system 500 is the data throughput is so low it doesn't really matter if having a weak signal, as there is hardly any bandwidth requirement to move data in other places. One could even take the data and send it over a 900 megahertz radio system that can be heard e.g. 2 miles away. There's number of different ways to achieve reliable data transmission. One way is using transmission equipment that jumps frequencies and when finding that frequency that has noise thereupon, the equipment will tell everybody to skip that frequency, and jump to a different one. Thus, the embodiments herein are adaptive to and can self-resolve interference problems. Accordingly, the embodiments herein are installable and workable in any type of physical structure.

It is also possible to track movement of the modules 280 as the residents wearing the modules 280 are e.g. walking down a hall and being handed off to the next access point 504. The access points 504 can track a resident by location in building or if they left the building, and can know that wearer of the module 280 is not a nurse but instead is a resident. So tracking is another thing that that can be accomplished by knowing which access point 504 reported, and where they are within the mesh network 590.

A typical BlueTooth module is very power efficient especially if doing an advertisement only every 15 seconds. Within the module 280, it's the various sensors that cause problems with power consumption, not the Bluetooth. The access points 504 are receiving their main power from the wall, so battery-charging and power considerations of the access points 504 are not an issue. Further, in the event of catastrophic power issues, all workers and facilities can always check the diaper on the invention the old-fashioned way, by looking, or by using existing on-premise hand-held devices e.g. a smart phone. Thus, the embodiments herein are effective whether they're under power or not.

HIPAA and Data Abstraction

The system 500 is designed to seldom communicate HIPAA and medical information. Within the embodiments herein, medical security of information is paramount, particularly if an individual goes into a critical state or something traumatic. From the garment 200 through the access points 504 to the server 508 there is no patient information transmitted, everything is abstracted. When the information finally gets to the web application 520, one can associate that unique number with patient information, so that's where it's all controlled. As such, the system 500 avoids HIPAA violations and/or private medical data breaches.

Meanwhile, within the database 512, there can be whatever designation per module 280, abstracted out to protect human identity, so the information has no connotation and doesn't look like it could be converted. For example, a unique database key per module could be a room number, not a resident's name. Such configurability allows the nursing home to do whatever is necessary to protect residents but also comply with HIPAA.

It is also possible as encrypt everything in the data so that it's binary, thus not a textual format. A hacker or data breacher could look at binary data but only see symbols, so unless someone understands what the symbols mean, they couldn't decode or breach that binary data.

There may come a time when some information transmitted might been a medical record or might be considered a HIPAA matter, but the embodiments herein are largely directed towards the information being safely transmitted and used as a management tool.

Economics of the System 500

One key focus of the system 500 is to get personnel to change their work habits. The garment 200 itself, the physical object, is arranged so that facilities will not be affected in terms of profitability. The garments 200 are going to be literally the same cost as what facilities are buying now.

At present, briefs in a nursing home are filled with a super absorbent polymers and thickness and bulkiness, in order to make those briefs hold urine output of a typical person for longer than most regulations stipulate. Nursing home workers are supposed to change patients every two hours, but this seldom occurs. So, brief manufacturers had been selling products on the basis of absorbency. The embodiments herein will substantially alter and improve this business model.

Further, the embodiments herein will inform workers when to change the garments 200, right to the minute. This provides a more comfortable experience for the resident.

Usually, briefs are the single largest disposable item single largest medical supply that nursing homes purchase. The only supply item larger than briefs is food. Consequently, the system 100 resolves known problems within a typical nursing home or residential facility business model.

The embodiments herein are designed to produce incontinence garments in high volumes, in multiple sizes, partly by reducing the amount of filler and some of the sophistication. Some of the sophisticated polymer will still be present, but the amount will be reduced.

The patient data and worker data being collected is advantageous for operators and owners of facilities. Analyzing this data could be a game changer. The most important things how the data gets from the garment 200 to the server 508 or cloud. As stated, there's a number of different ways to achieve this.

Using the embodiments herein, facilities will learn a lot about their workflow that they didn't previously know. The biggest resistance may be the caregivers, because the embodiments herein will point out their flaws, and will note the workers who are constantly late to residents and\or not giving residents the right treatment. The system will show that they are not doing their job very well, and will thus put a magnifying glass on them.

Another way to look at it is that some seemingly weak employees are not weak, but instead are improperly utilized. For example, maybe these workers just don't have the tools to be effective. For example, a typical State, e.g. Ohio, mandates checking the patients every 2 hours. This mandate is largely ignored as impractical and unenforceable, and thus is not a reflection on any particular worker. Other aspects of patient care get ignored also. However, with the system 500 in place, such a mandate is actually achievable. Specifically, as discussed earlier, the issue of an employee checking 3 garments versus checking 20-30 garments is but one example of increased efficiency and tracking accorded by the system 500.

There are some facilities that don't want the Nurses' Aides making the decision about exactly what is the threshold for being considered "wet", so they make a blanket rule saying "change the brief every 2 hours". They're probably not actually doing this task every 2 hours. This is also very inefficient, costly, wasteful, and in some cases disturbing to the patient.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations, or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations, or equivalents. It is intended that the following claims define the scope of the invention and that methods and structures within the scope of these claims and their equivalents be covered thereby.

What is claimed is:

1. A method of positioning and configuring a plurality of Graphical User Interfaces (GUIs) to be used in reporting and management of resident conditions, comprising:

structuring a plurality of GUIs to assist in data supervision by an institution housing a plurality of residents having a variety of different physical conditions, tolerances, and thresholds;

assembling a plurality of modules which sense resident information, where each module is associated with a specific resident;

the plurality of GUIs being responsive to a plurality of sensors which are located near to the resident;

configuring the plurality of GUIs to display information about the resident conveyed through the sensors and a plurality of access points;

providing a hydration GUI displaying a state of a resident's hydration meaning how long since a resident had a drink; and triggering a hydration alert if a predetermined amount of time programmed for a resident has elapsed and yet the resident has not generated a moisture alert as this may be an indication of a dehydration condition.

2. The method of claim 1, further comprising:
providing a vitals GUI enabling a user to view a plurality of statistics and vitals of the residents associated with the plurality of modules on an individual or group basis.

3. The method of claim 1, further comprising:
providing a MAC (Media Access Control) GUI displaying a MAC address of the module that is supplying data associated with a specific resident, where each module has its own MAC address.

4. The method of claim 1, further comprising:
providing a resident GUI displaying a unique resident identifier associated with the module indicated in the MAC address, the unique resident identifier comprising any of a name, room number, or internal identification value.

5. The method of claim 1, further comprising:
providing a moisture GUI displaying a current moisture content of any specific resident's brief in a percentage format.

6. The method of claim 1, further comprising:
providing a temperature GUI displaying a current temperature of a resident.

7. The method of claim 6, further comprising:
providing a temperature alarm corresponding with a resident's temperature when it falls below or rises above an adjustable, predetermined level;
the GUI displaying not only a current temperature but also a number of minutes that a temperature alarm (if it exists) has been active.

8. The method of claim 1, further comprising:
providing a position GUI displaying a current position of a resident based on the orientation of the module attached to a garment;
the positions comprising one of back, stomach, left side, right side, standing, and invalid.

9. The method of claim 1, further comprising:
providing an alert GUI displaying a plurality of alerts based on patient alarm conditions, where an alarm is a patient condition and an alert is a possible event resulting from that condition.

10. The method of claim 9, further comprising:
routing the plurality of alerts not only through the alert GUI but also through a plurality of pagers in which a pager is also assigned to one of a plurality of worker classes, supported classes comprising charge nurse, floor nurse, or certified nurse's assistant;
wherein the alerts are configured to notify a specific worker class based on the type of alert.

11. The method of claim 1, further comprising:
providing a hygiene GUI displaying a state of a resident's hygiene;
configuring the resident modules to trigger a hygiene alarm when the time to clear a moisture alarm is less than a time programmed in the system for that resident; and
the hygiene alert providing a warning through the hygiene GUI that the cleanup of a resident's soiled brief may not be adequate.

12. The method of claim 1, further comprising:
providing a moisture GUI displaying a moisture level within a resident's garment;
configuring the system to maintain information per resident on the occurrences of moisture alerts, including an expected time between moisture alerts based in historical data for that patient;
monitoring for and if appropriate, triggering a moisture alert indicating that a resident has a soiled brief from either urine or a bowel movement;
monitoring for and if appropriate, triggering a non-moisture alert suggesting that a pre-configured time has elapsed without a moisture alert for the resident thereby notifying staff of a possible dehydration condition of the resident.

13. The method of claim 1, further comprising:
providing a contact GUI displaying a state of a connection of the module to the garment comprising one of OK (Okay), ajar, or disconnected;
facilitating detection of a module not being worn by a patient by monitoring temperature data or motion data.

14. The method of claim 13, further comprising:
the access points tracking movement of the modules and thereby the residents wearing the modules; thereby determining if a resident is out-of-bed and walking down a hall where their signal is being handed off to a nearby next access point;
tracking a resident by their location in a building or if they left the building;
determining whether a wearer of the module is not a resident instead is a nurse or other health care professional.

15. A method of structuring and coordinating a residential and patient management system, comprising:
a plurality of access points continually receiving a plurality of resident data sent by a plurality of modules in which there is one module per resident;
the plurality of access points continually advertising the resident data to a server or to a cloud-based system;
the server or cloud-base software analyzing the data and continually updating a database, the database containing a variety of information about each resident as well as about a facility containing the residents;
the plurality of access points being plugged into wall outlets and thus always under power;
the plurality of access points tracking the advertisements, extracting data within those advertisements, and sending that data to the server;
notifying and informing workers when to change a patient garment at a granularity of every minute, thereby providing a more comfortable experience for the resident and also increasing efficiency of the workers;
providing a hydration GUI displaying a state of a resident's hydration meaning how long since a resident had a drink; and
triggering a hydration alert if a predetermined amount of time programmed for a resident has elapsed and yet the resident has not generated a moisture alert as this may be an indication of a dehydration condition.

16. The method of claim 15, further comprising:
a plurality of pagers in which a pager is also assigned to a class, or nurse role with supported classes comprising charge nurse, floor nurse, or certified nurse's assistant;
wherein the alerts are configured to notify a specific class of worker based on the type of alert.

17. The method of claim 15, further comprising:

assigning the plurality of access points a fixed IP address by the server when those access points power up;

the server putting an entry into the Structured Query Language (SQL) database.

18. The method of claim 15, further comprising:

categorizing residents and resident data in specific predetermined groups;

organizing the resident group-data by facility, or by groups of facilities, or by corporation;

monitoring the resident group-data for predetermined trends and determining whether a trend is across a certain type of facility, or across an entire corporation;

collecting high volumes of resident data relating bowel and bladder functioning in a variety of resident population configurations;

relating and assessing the high volumes of resident data to outcomes known to be of concern such as Urinary Tract Infections (UTIs) or bowel impactions.

19. The method of claim 15, further comprising:

in a building structure which may be signal-resistant, mesh network routing signals through a wired network, repeaters, or radio frequency mechanisms.

\* \* \* \* \*